(12) United States Patent
Kroll

(10) Patent No.: US 9,713,727 B2
(45) Date of Patent: Jul. 25, 2017

(54) CARDIAC-SAFE ELECTROTHERAPY METHOD AND APPARATUS

(71) Applicant: Galvani, Ltd., Edina, MN (US)

(72) Inventor: Mark W. Kroll, Crystal Bay, MN (US)

(73) Assignee: Galvani, Ltd., Edina, MN (US)

(*) Notice: Subject to any disclaimer, the term of this patent is extended or adjusted under 35 U.S.C. 154(b) by 231 days.

(21) Appl. No.: 14/228,694

(22) Filed: Mar. 28, 2014

(65) Prior Publication Data
US 2014/0296930 A1 Oct. 2, 2014

Related U.S. Application Data

(60) Provisional application No. 61/853,113, filed on Mar. 29, 2013.

(51) Int. Cl.
*A61N 1/378* (2006.01)
*A61N 1/39* (2006.01)

(52) U.S. Cl.
CPC ......... *A61N 1/3987* (2013.01); *A61N 1/3906* (2013.01)

(58) Field of Classification Search
CPC .. A61N 1/3627; A61N 1/3962; A61N 1/3987; A61N 1/3906
See application file for complete search history.

(56) References Cited

U.S. PATENT DOCUMENTS

| | | |
|---|---|---|
| 4,407,288 A | 10/1983 | Langer et al. |
| 5,314,448 A * | 5/1994 | Kroll .................... A61N 1/3956 607/5 |
| 5,391,186 A | 2/1995 | Kroll et al. |
| 5,405,363 A | 4/1995 | Kroll et al. |
| 5,607,454 A | 3/1997 | Cameron et al. |
| 5,700,281 A | 12/1997 | Brewer et al. |
| 5,735,876 A | 4/1998 | Kroll et al. |
| 5,782,883 A | 7/1998 | Kroll et al. |
| 5,871,510 A | 2/1999 | Kroll et al. |
| 6,577,102 B1 | 6/2003 | Vaisnys et al. |

(Continued)

FOREIGN PATENT DOCUMENTS

| | | |
|---|---|---|
| EP | 0617980 A2 | 10/1994 |
| EP | 1614446 A2 | 1/2006 |

OTHER PUBLICATIONS

International Search Report and Written Opinion for International Application No. PCT/US2014/032163 dated Aug. 12, 2014.

(Continued)

*Primary Examiner* — Michael D Abreu
(74) *Attorney, Agent, or Firm* — Patterson Thuente Pedersen, P.A.

(57) ABSTRACT

A multi-modal electrotherapy apparatus including circuitry for administering defibrillation therapy and for administering medium voltage therapy (MVT) adapted to reduce the side effects of MVT. The electrotherapy apparatus is configured to selectively deliver MVT to vectors not involving the ventricles and defibrillation therapy to vectors involving the ventricles. The apparatus can use biphasic waveforms configured to avoid capture of cardiac cells during MVT. The electrotherapy apparatus can minimize the risk of applying MVT at inappropriate times, such as during atrial fibrillation or where conventional ventricular tachycardia or ventricular fibrillation therapy is more appropriate.

8 Claims, 23 Drawing Sheets

(56) References Cited

U.S. PATENT DOCUMENTS

| | | |
|---|---|---|
| 6,760,621 B2 | 7/2004 | Walcott et al. |
| 7,383,085 B2 | 6/2008 | Olson |
| 8,401,637 B2 | 3/2013 | Kroll et al. |
| 8,483,822 B1 | 7/2013 | Gilman et al. |
| 8,750,990 B1 | 6/2014 | Gilman et al. |
| 8,805,495 B2 | 8/2014 | Gilman et al. |
| 8,868,178 B2 | 10/2014 | Gilman et al. |
| 2002/0133205 A1 | 9/2002 | Walcott et al. |
| 2007/0250124 A1 | 10/2007 | Burnes et al. |
| 2008/0051843 A1 | 2/2008 | Li et al. |
| 2010/0145400 A1 | 6/2010 | Kim et al. |
| 2011/0166613 A1 | 7/2011 | Li et al. |
| 2013/0035735 A1 | 2/2013 | Kroll |
| 2014/0236248 A1 | 8/2014 | Gilman et al. |
| 2014/0336718 A1 | 11/2014 | Gilman et al. |
| 2015/0032170 A1 | 1/2015 | Gilman et al. |

OTHER PUBLICATIONS

European Application No. 14774242.3, EP Search Report dated Nov. 18, 2016.

\* cited by examiner

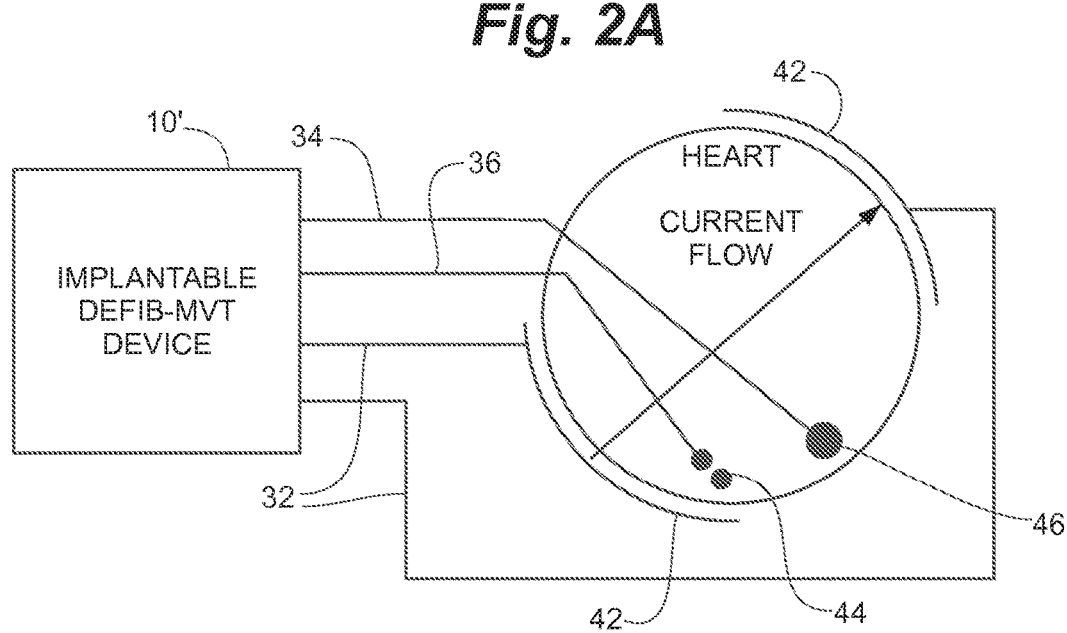

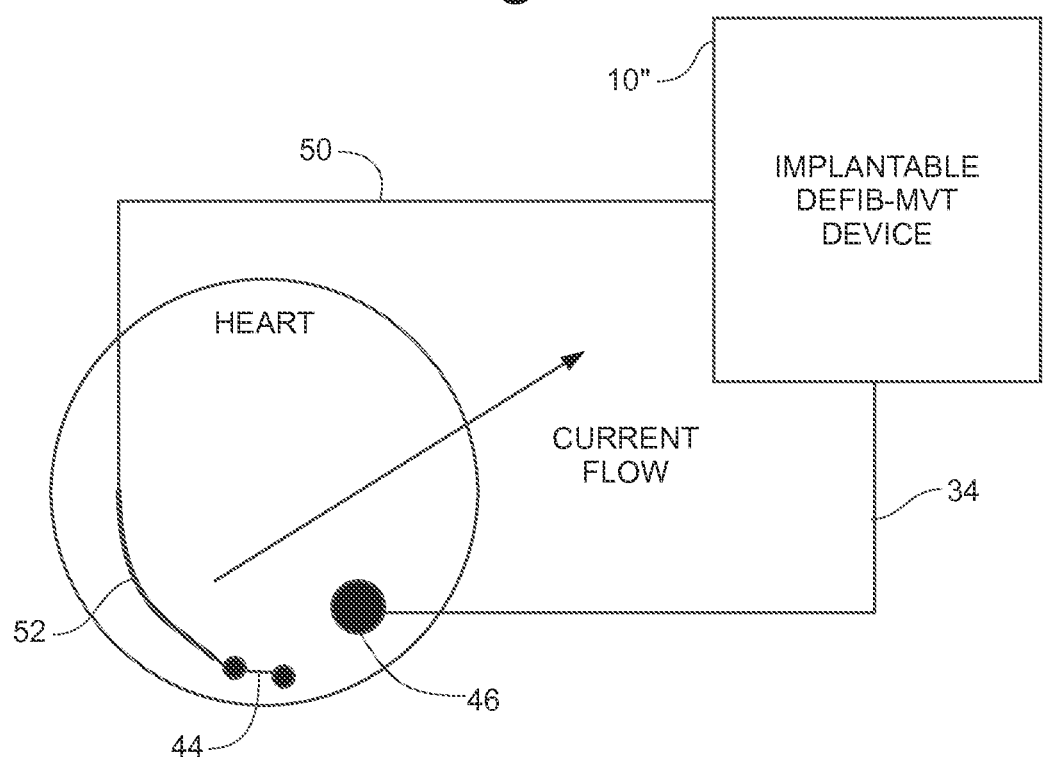

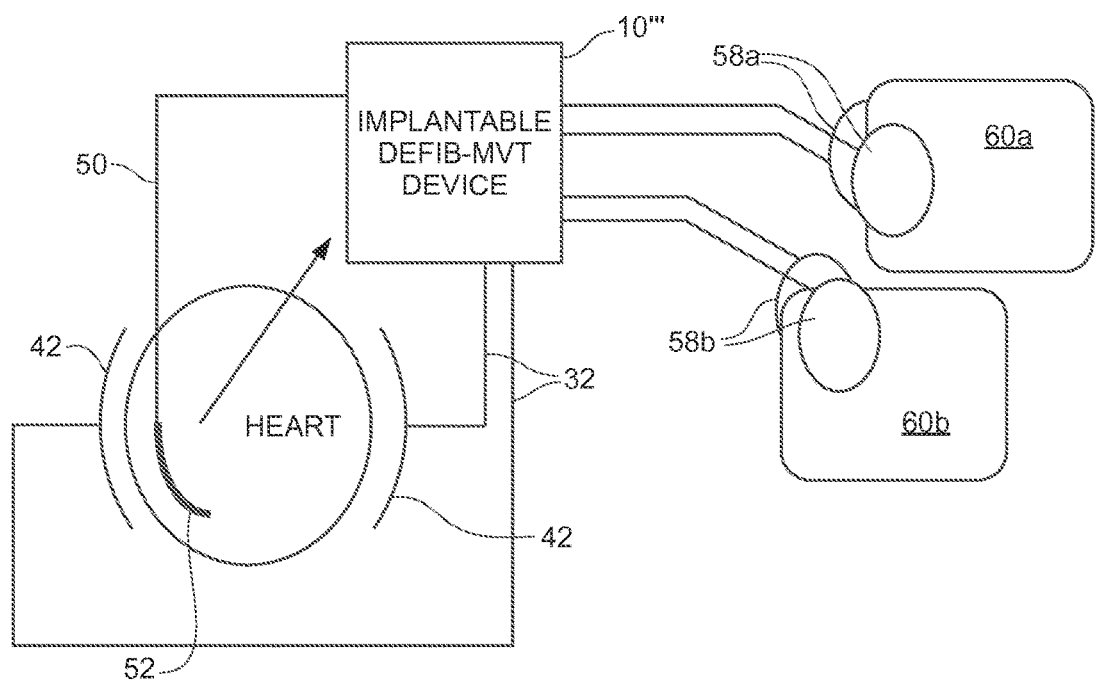

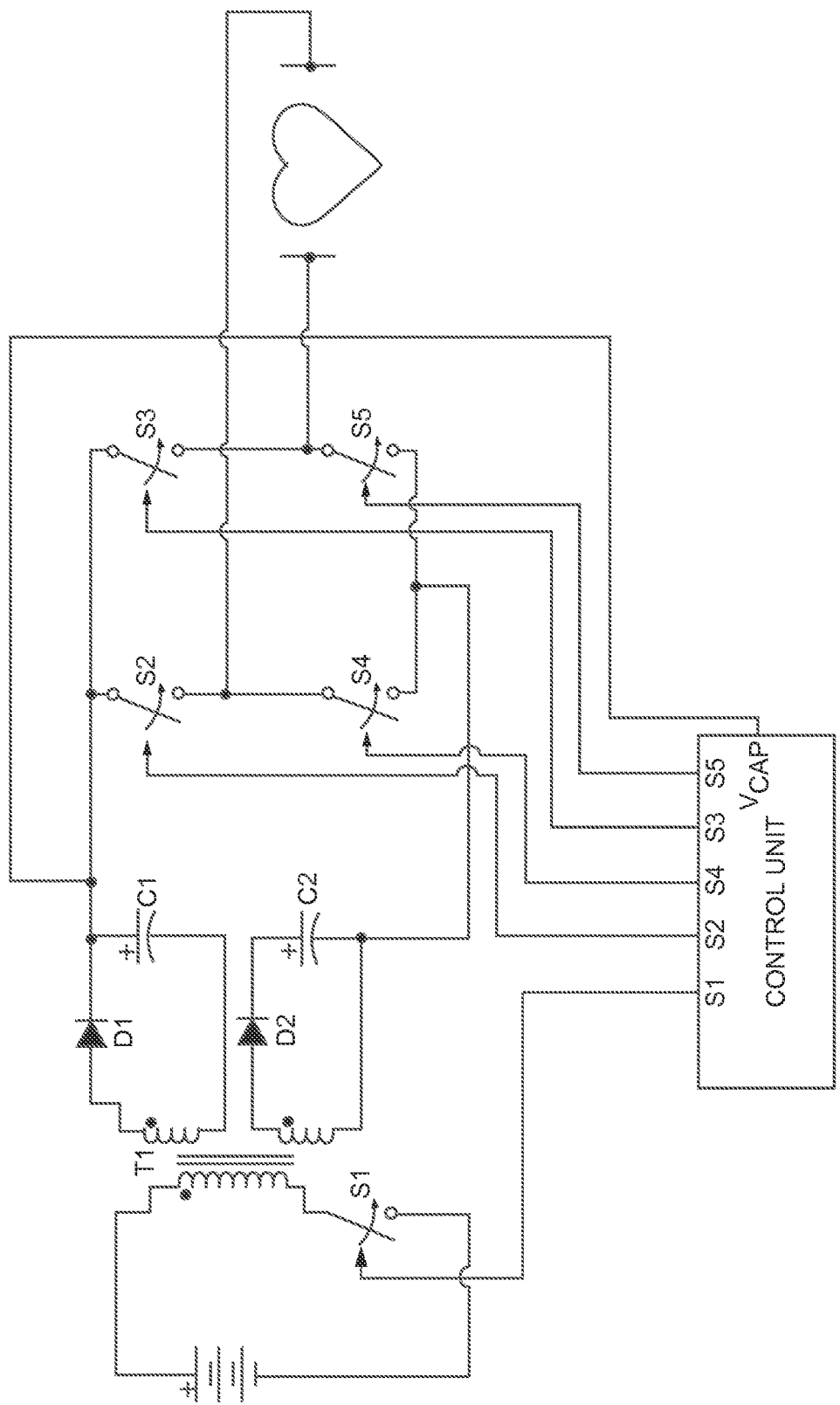

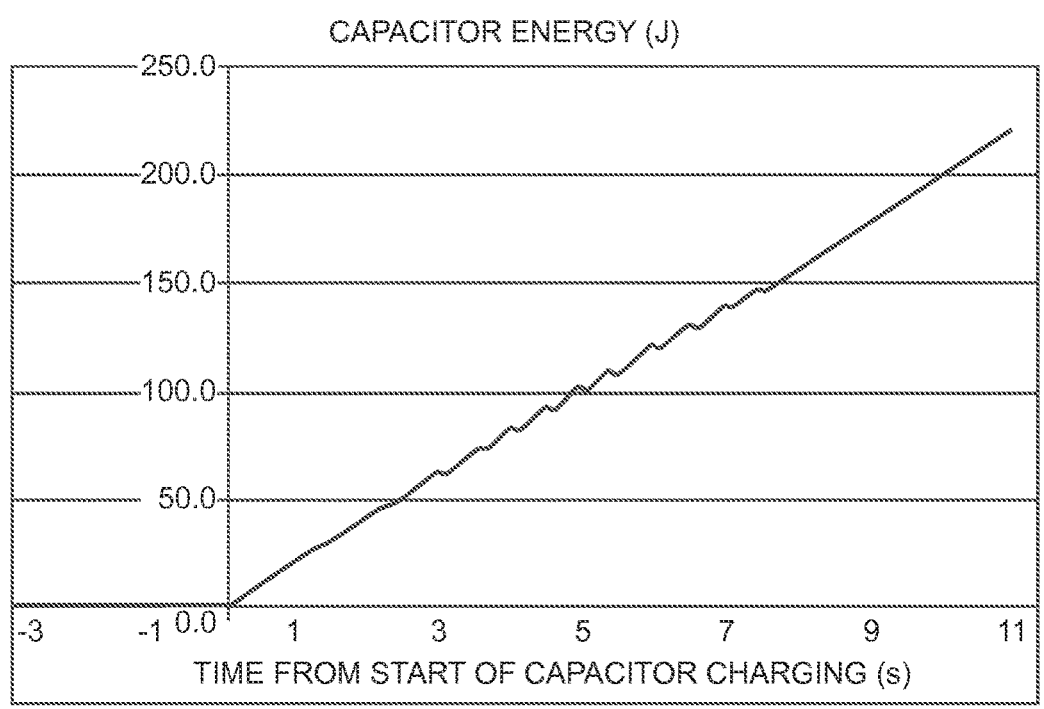

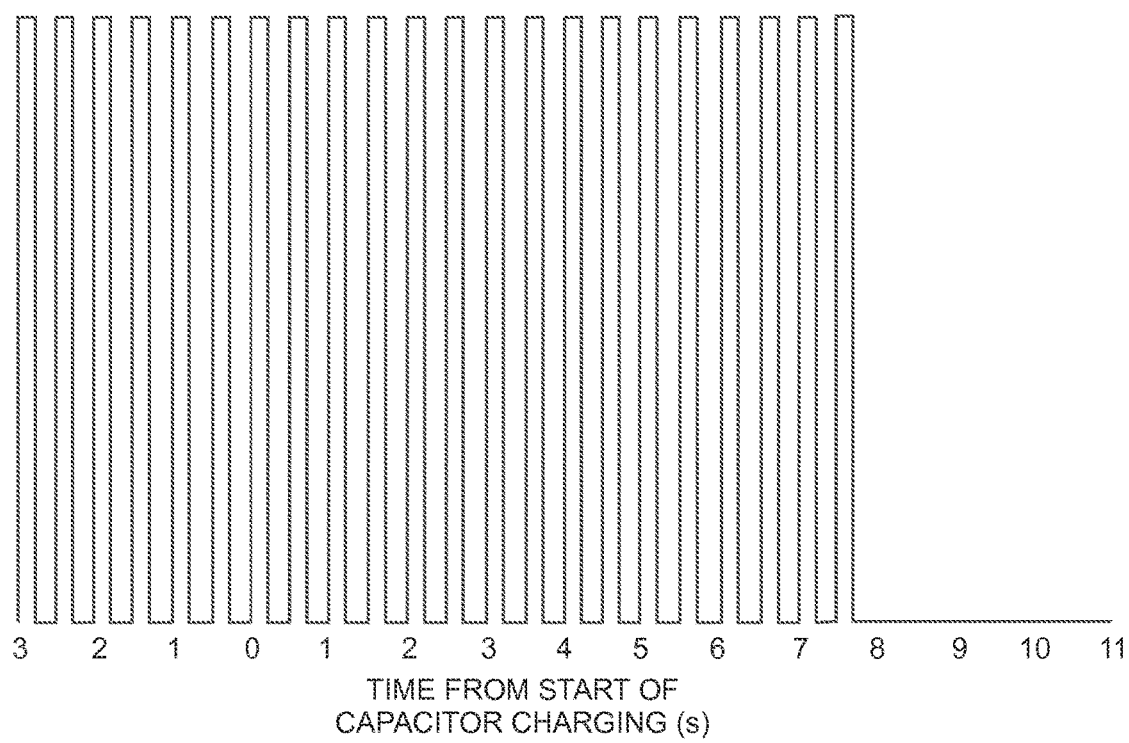

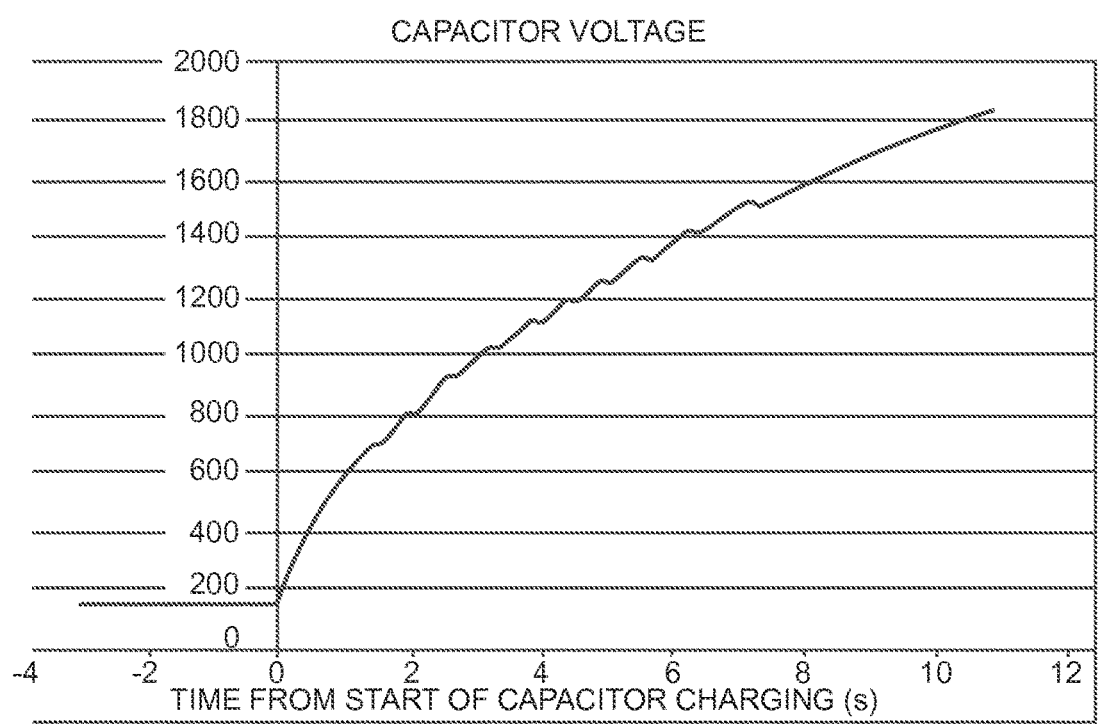

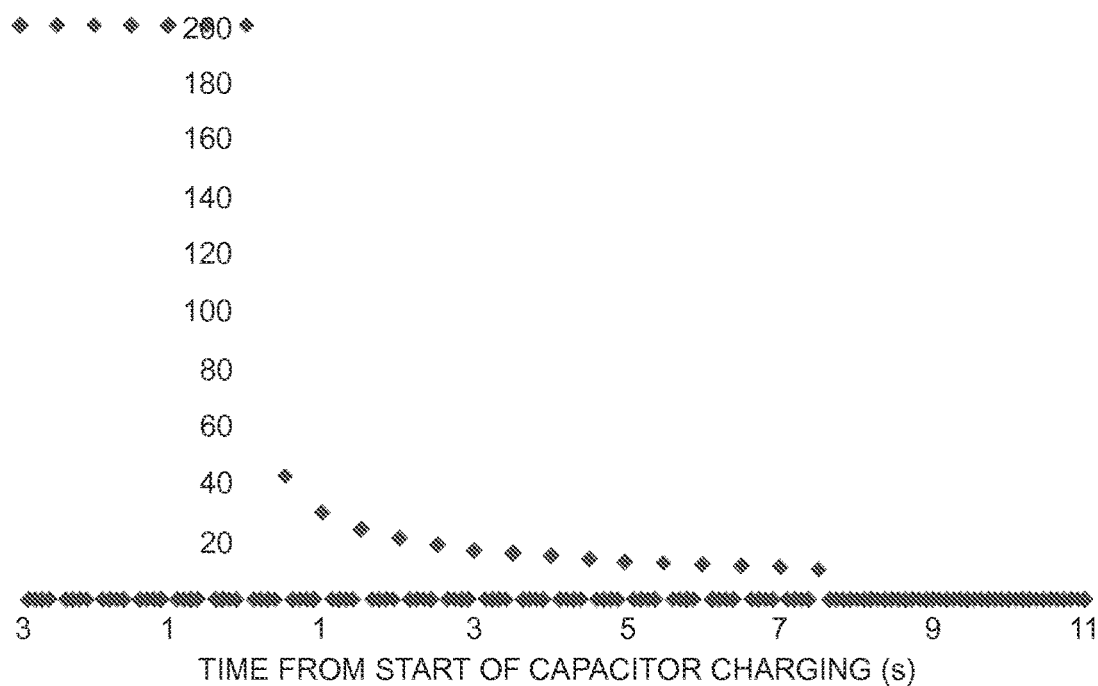

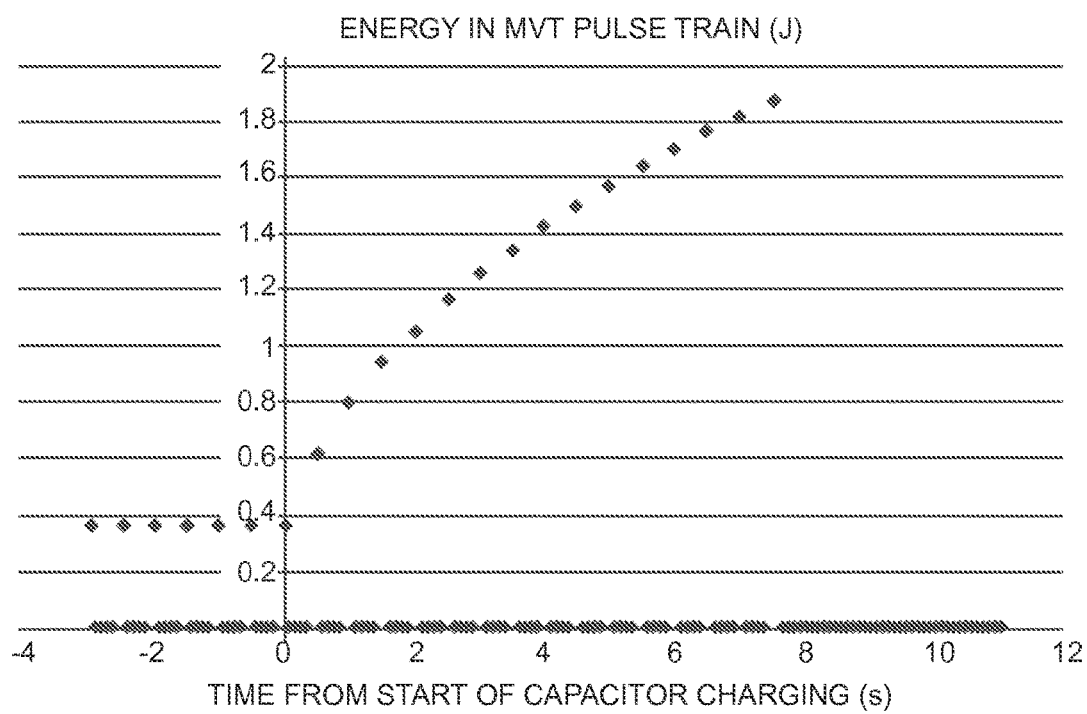

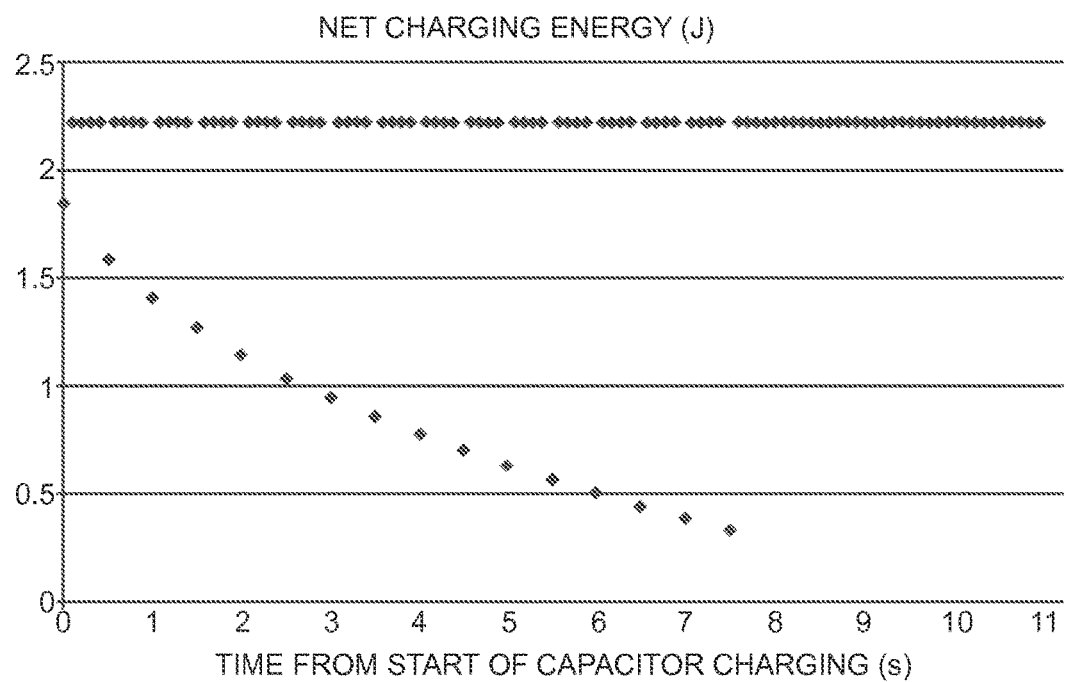

MVT WAVEFORM

MVT WAVEFORM

CARDIAC-SAFE ELECTROTHERAPY METHOD AND APPARATUS

PRIOR APPLICATION

This application claims the benefit of U.S. Provisional Application No. 61/853,113, filed Mar. 29, 2013, entitled "Cardiac Safe Electrotherapy Method and Apparatus," which is incorporated by reference herein.

FIELD OF THE INVENTION

The invention relates generally to treatments for individuals experiencing cardiac arrest and, more particularly, to implantable or external treatment apparatus and associated methods of operation thereof, incorporating medium voltage therapy (MVT) with defibrillation therapy.

BACKGROUND OF THE INVENTION

Cardiac arrest is a significant public health problem cutting across age, race, and gender. Defibrillators have had a major impact on dealing with cardiac arrest in that they are the only reliable treatment for VF (ventricular fibrillation).

A positive impact on cardiac arrest survival has been demonstrated with the substantial reduction in time to defibrillation provided by the widespread deployment of automated external defibrillators (AEDs) and the use of implantable cardioverter defibrillators (ICDs). Examples of AEDs are described in U.S. Pat. Nos. 5,607,454, 5,700,281 and 6,577,102 while examples of ICDs are described in U.S. Pat. Nos. 4,407,288, 5,391,186, 5,405,363, and 7,383,085.

Research has been clear in demonstrating that the timing of resuscitation is of critical importance. For example, the probability of recovery goes down by about 5% per minute after the onset of ventricular fibrillation (VF) from a non-electrocution cardiac arrest. This knowledge led to the recent widespread deployment of AEDs, primarily in public areas with a high population concentration such as airports and shopping malls. A positive impact on cardiac arrest survival has been demonstrated due to the substantial reduction in time to defibrillation as a result of more available access to AEDs. In addition, for those patients identified as being at particularly high risk, an implantable cardioverter-defibrillator is often implanted in order to address episodes of cardiac arrest without the involvement of a rescuer.

One major challenge in the use of widely-deployed defibrillators is that defibrillation of a heart that has been in VF for a while can actually harm the heart. When the heart has been in VF for a long time, the delivery of the shock can actually lead to more dangerous rhythms such as asystole or EMD (Electro Mechanical Disassociation, a.k.a. Pulseless Electrical Activity or PEA). These problems occur after cardiac arrest because without continuing blood flow the oxygen and energy supplied to the heart tissue is no longer sufficient to enable it to contract with the necessary force to move blood in the case of PEA; and in the case of asystole can no longer even conduct an electrical signal. Shocking a heart in this condition is unlikely to result in a pulsatile rhythm.

In the case of VF, performing CPR-type chest compressions before defibrillation and minimizing the time to defibrillation shock following the cessation of the CPR chest compressions is important in facilitating effective recovery especially in cases of long duration VF. The primary purpose of administering cardio-pulmonary resuscitation (CPR) to a cardiac arrest victim is to cause blood to circulate into the heart before shocking it. This provides two benefits: first, the distended right ventricle is compressed back to its more nearly normal size, facilitating more effective defibrillation; second, the heart tissue has the potential to become more oxygenated in order to work effectively. Despite the importance of CPR-type chest compressions, they are often not performed in the field for a variety of reasons.

One approach that has been proposed for automating a treatment that can provide an effect similar to performing chest compressions is with the application of cardiac electrotherapy stimuli having an amplitude that is greater than that of pacing-type stimuli, but less than the amplitude and energy level associated with defibrillation-type stimuli. These are known in the art as medium voltage therapy (MVT). For example, U.S. Pat. No. 5,314,448 describes delivering low-energy pre-treatment pulses followed by high-energy defibrillation pulses, utilizing a common set of electrodes for both types of stimuli. According to one therapeutic mechanism of this pre-treatment, the MVT pulses cause chest constrictions similar to those of manual chest compressions of traditional CPR. The constrictions provide fresh oxygenated blood to the heart and facilitate a greater probability of successful defibrillation with a follow-on defibrillation pulse. U.S. Pat. No. 6,760,621 describes the use of MVT as pretreatment to defibrillation that is directed to reducing the likelihood of PEA and EMD conditions as a result of the defibrillation treatment. The mechanisms by which these results are achieved by MVT include a form of sympathetic stimulation of the heart. These approaches are directed to influencing the electrochemical dynamics or responsiveness of the heart tissues.

MVT has also been recognized as a way of forcing some amount of cardiac output by electrically stimulating the heart directly with stimuli that cause some heart and some skeletal muscle to contract in a controlled manner. See U.S. Pat. Nos. 5,735,876, 5,782,883 and 5,871,510. These patents describe implantable devices having combined defibrillation, and MVT capability for forcing cardiac output. U.S. Pat. No. 6,314,319 describes internal and external systems and associated methods of utilizing MVT to achieve a hemodynamic effect in the heart as part of an implantable cardioverter defibrillator (ICD) for purposes of achieving a smaller prophylactic device. The approach described in the '319 patent uses the MVT therapy to provide a smaller and less expensive implantable device that can maintain some cardiac output without necessarily providing defibrillation therapy.

Unlike a conventional AED or ICD, which operate with the primary purpose of restoring a normal cardiac rhythm, MVT stimulation can be used to provide cardiac output, which in turn causes perfusion of the heart and brain, as well as other critical body tissues. By providing perfusion of the heart and other vital organs, MVT prolongs the life of the patient even while the patient continues experiencing the arrhythmia. Additionally, MVT improves the likelihood of successful defibrillation or of a spontaneous return of circulation. An AED equipped with MVT can provide consistent high quality chest compressions. In the case of an implanted ICD, backup chest compressions provided by MVT can, in one sense, be even more important than in an AED, since in the case of the implantable device there may be no rescuer available to perform CPR when needed.

As heretofore envisioned, a combined defibrillation-MVT device utilizes separate defibrillation and MVT circuitry for generating and applying each type of electrotherapy since the magnitudes of these treatments can differ by an order of magnitude or more. Unfortunately, a number of challenges remain in practically incorporating MVT into defibrillation devices. Thus, improvements to a combined defibrillation-MVT device would be desirable.

SUMMARY OF THE INVENTION

The invention is directed generally towards improving the safety and efficacy of medium voltage therapy (MVT) when used in combination with defibrillation. Improvements can be accomplished by protecting cardiac functionality by various aspects as described herein, alone or in any combination with other aspects, such as directing MVT and defibrillation therapies along different vectors, delivering MVT pulses shaped to avoid capture of cardiac cells, and withholding MVT unless there is a high confidence that the patient is experiencing PEA or ventricular fibrillation.

One aspect of the invention is directed to a multi-modal electrotherapy apparatus, either implantable or external to a patient, for treating a patient experiencing a potential arrhythmia. The two modes of MVT and defibrillation. The MVT has energy and waveform characteristics to force repeated mechanical compression of the patient's heart that causes hemodynamic perfusion in the patient; the defibrillation therapy has energy and waveform characteristics to defibrillate the heart. The apparatus is constructed such that defibrillation pulses are directed, through patient terminals (e.g. electrode coils or electrode pads), to a vector that includes at least one electrode proximate the right ventricle of the patient's heart and the MVT pulses are directed to a vector that omits electrodes proximate the right ventricle.

Another aspect of the invention is directed to pulse shaping circuitry within the electrotherapy apparatus which is adapted to generate a biphasic waveform with a first phase less than 50 microseconds in duration.

Another aspect of the invention is directed to withholding MVT pulses based on the patient's heart rate and the presence of cardiac output as detected by a hemodynamic sensor. MVT is withheld when cardiac output is present. MVT is applied when cardiac output is not present and the patient's heart rate is within a normal range. MVT is also applied when the patient's heart rate is very fast and cardiac output is not present after the application of conventional ventricular tachycardia/fibrillation therapy.

Another aspect of the invention is directed to the use of one or more atrial fibrillation discriminators, adapted to distinguish between atrial fibrillation and ventricular fibrillation with predefined confidence levels. The apparatus can withhold MVT unless a majority of atrial fibrillation discriminators reports a high confidence that ventricular fibrillation is present.

A number of advantages will become apparent from the following Detailed Description of the Preferred Embodiments.

BRIEF DESCRIPTION OF THE DRAWINGS

The invention may be more completely understood in consideration of the following detailed description of various embodiments of the invention in connection with the accompanying drawings, in which:

FIGS. 2A-2C illustrate various examples of electrode arrangements for implantable MVT devices such as the device of FIG. 1 according to various embodiments.

FIG. 4 is a simplified circuit diagram depicting the primary components of an exemplary charging and discharging circuit according to one embodiment.

FIG. 6 illustrates how the capacitor energy increases with time according to an implementation in one type of embodiment in which MVT is applied during charging of the capacitor.

FIG. 7 illustrates timing of the MVT pulse trains while the main capacitor undergoes charging according to one example embodiment.

FIG. 8 is a chart depicting the capacitor voltage in an embodiment that applies MVT during charging for defibrillation.

FIG. 9 is a chart depicting the MVT pulse duration as a function of time for an embodiment in which successive pulses are progressively narrowed as the capacitor voltage is increased during charging.

FIG. 10 is a chart illustrating the energy cost of delivering the stimulation charge by using narrow pulses of higher voltage according to one embodiment.

FIG. 11 is a chart illustrating the net charging energy per 0.1 second (100 ms) period according to one embodiment.

Figure 1:
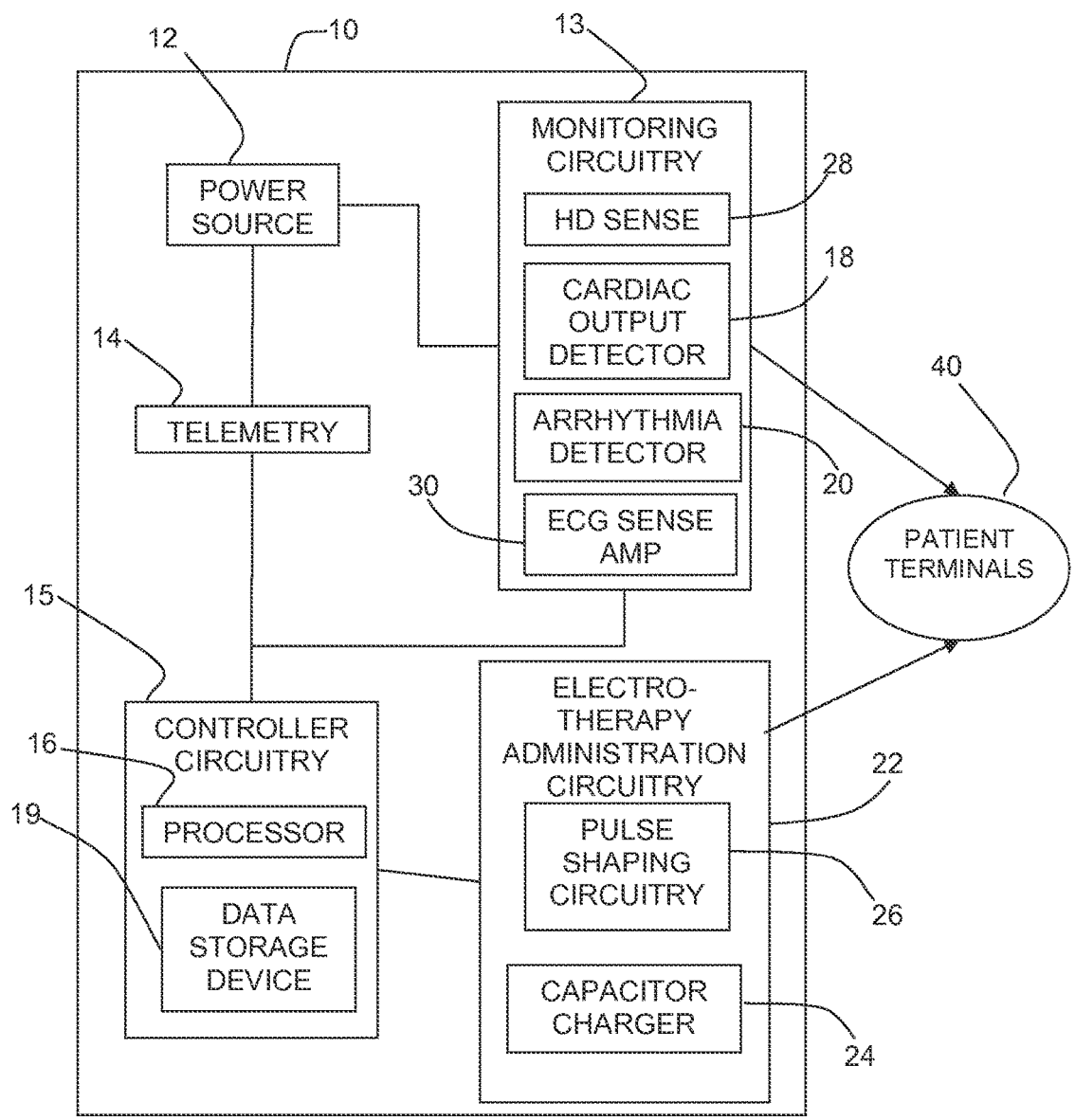
FIG. 1 is a diagram illustrating the sub-systems of a device enabled with medium voltage therapy (MVT) facilities, according to one embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENTS

Aspects of the invention are directed to apparatus and methods for applying electrotherapy to treat one or more types of arrhythmias in a patient. The electrotherapy is automatically applied by a device, either implantable or external to the patient, that provides electrotherapy of at least two modalities: defibrillation therapy, and medium voltage therapy (MVT). Defibrillation therapy involves the use of high-voltage pulses to fully reset the electrical activity within the heart, after which a normal sinus rhythm can be restored (without re-entrant activity of propagating action potential waves).

MVT involves stimulation of muscle cells in the heart, elsewhere in the upper body, or both, so that those muscle cells are forced to contract and relax repeatedly in a controlled manner. To force each contraction, MVT is of a sufficient charge level and pulse rate to overwhelm the body's natural control of these muscles to force the contraction of relaxed (i.e. non-captured) muscle cells while maintaining already captured muscle cells in their contracted states.

Insofar as heart muscle is concerned, MVT can be said to directly capture a substantial portion of myocardial cells, throughout the heart, rather than rely on a working natural mechanism of propagating waves of action potentials. MVT differs considerably from pacing therapy in this regard. Pacing involves applying a small stimulus to a specific part of the heart, to trigger a somewhat naturally-propagating wave of action potentials. Instead, MVT applied to heart muscle does not rely on a working mechanism of action potential propagation. In MVT, myocardial cells throughout the heart, (though not necessarily all of the myocardium) are captured at the same time as a burst of MVT charge is applied to those cells, forcing the captured muscle cells to contract simultaneously (i.e., not in a sequence as is the case with a natural sinus rhythm or in response to a pacing pulse). A sufficient quantity of cells is captured by MVT to produce a positive hemodynamic effect that is similar to what may be achieved in a CPR-type chest compression.

MVT also differs from cardioversion, which involves administering a single and closely-timed short-duration electrical shock to the heart during the R wave of the QRS complex, to terminate arrhythmias such as atrial fibrillation or ventricular tachycardia by momentarily interrupting the abnormal rhythm, allowing the heart's natural electrical system to regain normal control of the heart. Cardioversion pulses can be monophasic or biphasic, and each electrical pulse is applied once during each electrocardiogram (ECG) cycle with a duration on the order of milliseconds and generally only once per arrhythmia. MVT does not require there to be a discernable rhythm in the ECG to which the pulses must be synchronized. Also, MVT is applied in bursts of pulses, referred to herein as pulse trains, that are sustained for a much longer duration so that the captured muscle tissue is held in its contracted state, then released to relax, then again captured and maintained contracted. The purpose of MVT is not to reset the electrical activity of the heart; rather it is to force mechanical contractions without regard to whether the heart has a working electrical system capable of propagating waves of action potentials.

MVT applied to non-cardiac muscle, such as skeletal musculature, diaphragm, etc., causes contraction of these muscle tissues and mimics the effect of CPR-type chest compressions. Thus, MVT can contract the heart not only by directly capturing myocardial cells to electrically force their contraction, but also by electrically forcing non-cardiac cells in muscle tissue surrounding the heart to contract, thereby reducing the volume in the chest and mechanically compressing the heart.

MVT can therefore be used to cause perfusion of at least the heart, and potentially also the lungs, brain, and other critical organs, to prolong the life of a patient during a hemodynamically-compromising arrhythmia in which there is insufficient cardiac output to naturally sustain the life of the patient.

FIG. 1 is a block diagram illustrating an combined defibrillation-MVT device 10 constructed in accordance with one aspect of the invention. The device circuitry is electrically coupled to the patient terminals 40, which can then be electrically coupled with regions of the patient's upper body (not shown) via a series of leads such as an output lead, pressure sense lead, or ECG sense lead (leads not shown). The electronic circuit includes monitoring circuitry 13. The monitoring circuitry can include a conventional ECG amplifier 30 for amplifying cardiac signals. The amplified cardiac signals can be analyzed by a conventional arrhythmia detector 20 that determines if an arrhythmia is present. The arrhythmia detector 20 may be one of several types well known to those skilled in the art and is preferably able to distinguish between different types of arrhythmias, for example; fibrillation, tachycardia, and asystole.

Optionally, the monitoring circuitry contains a hemodynamic sensing section 28 which amplifies and conditions a signal from a one or more hemodynamic sensors such as, for example, a pressure sensor, a microphone, an ultrasonic blood flow sensor, an impedance plethysmography device, a pulse oximeter, a cardiac impedance sensor, or the like. The output of the hemodynamic sense circuit 28 is fed to a cardiac output detection circuit 18 that analyzes the data and determines an estimate of the cardiac output. Data from the arrhythmia detector circuit 20 and the cardiac output detection circuit 18 is fed to the controller circuitry 15, which can include a processor 16. This combination of inputs gives the ability to sense PEA as PEA is defined as the lack of cardiac output in the presence of otherwise normal heart rates.

An aspect of this invention is the use of the following algorithm:

1. If there is no cardiac output found from hemodynamic sensors then
2. Check the heart rate via the arrhythmia detector and
3. If the arrhythmia detector does not detect an arrhythmia then
4. Declare the presence of pulseless electrical activity (PEA)
5. Deliver PEA therapy The controller circuitry 15 determines if electrotherapy is appropriate, and what modality of the electrotherapy to apply at what time, i.e., defibrillation shock or MVT. Typically, MVT is applied close in time prior to application of the defibrillation shock. In one such embodiment, the defibrillation shock is applied within 30 seconds following cessation of the MVT. In a related embodiment, the time period between cessation of the MVT and the defibrillation is reduced to about 10 seconds. In a further embodiment, the time period between the cessation of the MVT and the application of the defibrillation is less than 5 seconds (e.g., 3 seconds). In another type of embodiment, the time period between cessation of MVT and application of the defibrillation shock is reduced to less than one second.

When electrotherapy is indicated, the controller circuitry 15 prompts the electrotherapy administration circuitry 22 to charge a capacitor within the via the capacitor charger 24.

The electrotherapy administration circuitry 22 directs the pulse shaping circuitry 26 to deliver the electrotherapy to the patient terminals 40. Notably, according to one aspect of the invention, the electrotherapy administration circuitry 22 including the capacitor charger 24, pulse shaping circuitry 26, including the capacitor, are used for preparing (i.e., charging) and applying both MVT and defibrillation electrotherapies. In a related aspect of the invention, the MVT can be administered while the capacitor charger 24 circuit prepares for administration of the defibrillation therapy.

The controller circuitry 16 may communicate with external sources via a telemetry circuit 14 within the device 10. The power for the device 10 is supplied by a power source 12 which could be an internal or external battery or other power sources as known in the art.

FIG. 2A is a diagram showing the connection of an implantable device 10' according to one embodiment to the heart as one of the regions in the patient's upper body 40 in an epicardial patch configuration. In this thoracotomy configuration, current passes through an output lead pair 32 to electrode patches 42 which direct the current through the heart. A pressure sense lead 34 passes the signal from an optional pressure transducer 46 that enables a measurement of blood pressure. The ECG is monitored by sense electrodes 44 and passed to the device 10' by a lead 36. In an example embodiment, the area of the electrodes 42 is between approximately 0.5 $cm^2$ and 20 $cm^2$ each.

FIG. 2B illustrates an example of a non-thoracotomy arrangement according to one embodiment. In this system, the current passes from a coil electrode 52 in the heart to the housing of the MVT device 10". An endocardial lead 50 combines the ECG sensing lead and the pulse output lead. The ECG is monitored by sense electrodes 44 in the heart and passes through the endocardial lead 50. There is an optional pressure transducer 46 that in one embodiment may be positioned in the heart, that passes a signal to the device 10" via optional lead 34.

FIG. 2C illustrates an implantable MVT device 10"" that supports a set of diverse electrode arrangements for selectively applying MVT to different areas of the patient. In addition to electrodes 42 and 52 discussed above in the thoracotomy and non-thoracotomy arrangements for directing defibrillation pulses and MVT through the myocardium, device 10"" further includes additional electrodes 58a and 58b for placement at specific locations in the patient's upper body, 60a and 60b, to direct MVT through non-cardiac muscles. Examples of locations 60a and 60b include (without limitation) locations for activating the pectoral muscles, intercostal muscles, the diaphragm (e.g., via stimulation of the phrenic nerve), and the abdominal muscles. The additional electrodes 58a and 58b, in various embodiments, have a variety of constructions and locations, including, for example, subcutaneous patch electrodes, one or more additional electronics/battery housings, intra-vascular leads, and the like. Placements include any suitable location such as, for example, subcutaneously at the base of the neck, in the azygos vein, in the cephalic vein, subcutaneously in the lower torso, and subcutaneously on one or both sides of the upper torso. In a related embodiment, the additional one or more of electrodes 58a and 58b are used for hemodynamic measurements such as, for example, electrical impedance plethysmography.

Figure 3:
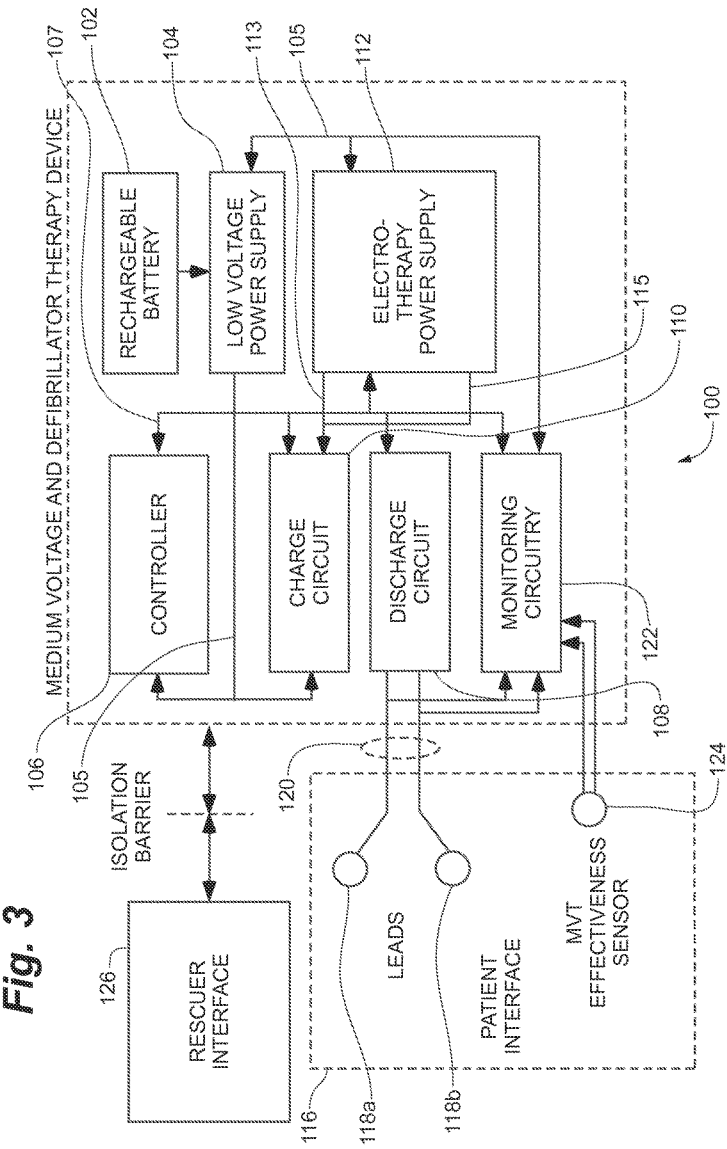
FIG. 3 is a diagram illustrating the sub-systems of an external device enabled with medium voltage therapy facilities, according to one embodiment.

FIG. 3 is a diagram illustrating an example AED 100 that utilizes MVT according to one embodiment. AED 100 can be a hand-portable instrument that is self-powered from an optionally-rechargeable battery 102. Battery 102 provides an energy source that can be converted and conditioned for powering the various circuitry of AED 100. A low voltage power supply 104 converts the battery power into one or more stabilized power supply outputs 105 for supplying the power to the subsystems of AED 100. The subsystems include a controller 106, for example a microprocessor that is programmed and interfaced with other subsystems to control most of the functionality of AED 100.

In the embodiments in which the controller 106 is implemented as a microprocessor or microcontroller, the microprocessor interface includes data and address busses, optional analog and/or digital inputs, and optional control inputs/outputs, collectively indicated at microprocessor interface 107. In one example embodiment, the microprocessor is programmed to control the sequence of the electrotherapy, as well as the output waveform parameters. The user input to the system can be in the form of simple pushbutton commands, or voice commands.

Example AED 100 includes a discharge circuit 108 for administering therapeutic stimuli to the patient. Discharge circuit 108 controls the release of therapeutic energy, in either the defibrillation, or MVT modalities, to achieve a desired stimulus having a particular waveform. Charge circuit 110 energizes discharge circuit 108 to achieve the desired output stimulus. Electrotherapy power supply 112 provides a sufficient energy source 113 to charge circuit 110 to enable charge circuit 110 and discharge circuit 108 to ultimately deliver one or more defibrillation pulses, and to deliver MVT, to an exterior surface of the patient.

Typically, a voltage sufficient to achieve a therapeutic defibrillation stimulus from the exterior of a patient is in the range of 1 kV-3 kV; whereas the typical range of voltages for externally-applied MVT is 100-1000 V. Notably, according to one aspect of the invention, charge circuit 110, and discharge circuit 108, are utilized for both modalities. In a related aspect of the invention, the MVT can be administered while the charge circuit 110 prepares for administration of the defibrillation therapy.

The defibrillation and MVT stimuli are administered to the patient via patient interface 116. In one embodiment, patient interface 116 includes electrodes 118a and 118b that are adhesively applied to the patient's chest area, typically with an electrically-conductive gel. Electrodes 118a and 118b are electrically coupled, such as by insulated copper wire leads 120, to discharge circuit 108. In one example embodiment, electrodes 118a and 118b can deliver the defibrillation stimuli and the MVT stimuli as well as obtain information about the patient's condition. For example, electrodes 118 can be used to monitor the patient's cardiac rhythm. Signals originating in the patient that are measured by electrodes 118 are fed to monitoring circuitry 122.

In one embodiment, patient interface 116 includes an MVT effectiveness sensor 124 coupled to monitoring circuitry 122. MVT effectiveness sensor 124 can measure observable patient characteristics that are related to the patient's condition, in like fashion to the hemodynamic monitoring and determining arrangements described above for an implantable embodiment.

AED 100 also includes a rescuer interface 126 operatively coupled with controller 106. In one embodiment, rescuer interface 126 includes at least one pushbutton, and a display device for indicating at least the operational status of AED 100. In a related embodiment, rescuer interface includes a system for providing visual or audible prompting or instructions to the rescuer. In another embodiment, rescuer interface 126 includes a plurality of human-operable controls for adjusting the various AED operational parameters, and a display device that indicates measurements made by monitoring circuitry 122.

FIG. 4 is a simplified circuit diagram depicting the primary components of an exemplary charging and discharging (i.e., output) circuit according to one embodiment. This type of charging and discharging circuit is applicable in either the implantable device or the external AED embodiments. In the simplified charging portion, battery B1 supplies current to the primary winding of transformer XMFR1 while switch S1 is operated in a periodic switching mode by the control unit. In each switching cycle, after switch S1 has been on sufficiently long to electro-magnetically charge transformer XMFR1, switch S1 is opened. The primary side of the transformer XMFR1 is magnetically coupled to the secondary windings and, by a turns ratio of n:m (with m being a multiple of n), the secondary side of transformer XMFR1 increases the voltage from the primary side. By the principle of conservation of energy, the energy delivered into the primary side of transformer XMFR1 must go some place and in this circuit it flows through diodes D1 and D2 to charge capacitors C1 and C2. For the sake of simplicity, several components unrelated to the basic functionality are omitted, such as a snubber network for absorbing voltage spikes produced by the primary winding when the switch S1 is opened. This type of charging circuit is well known in the art, as are a variety of adaptations, any of which may be suitable according to various embodiments. Other types of charging circuits may also be utilized, such as boost converters, charge pumps, etc. Notably, this charging circuit boosts voltages for both, the defibrillation energy, and the MVT.

The capacitive storage for the shock is depicted in FIG. 4 as a network of 2 capacitors in this schematic for simplicity. In a more practical embodiment, the system is realized with a set of 3-7 capacitors in series with suitable interconnections with the charging and discharging circuitry. Hereinafter, the capacitor bank may be referred to as simply, the "capacitor."

The discharge portion of this exemplary circuit is an H-bridge topology. Switches S2-S5 can be implemented utilizing suitable technology such as, for instance, solid state devices like FET devices, IGBT devices, SCR devices, and the like. In this simplified diagram, a number of components are omitted for the sake of brevity, as this H-bridge circuit topology is well-known. For instance, isolated driving circuits are generally used for controlling the upper H-bridge switches S2 and S3. Also, an anti shoot-through provision is generally employed to prevent both switches of a common leg of the H-bridge from being in their conductive states at any moment.

The control unit comprises one or more control circuits such as at least one microcontroller, state machine, or microprocessor systems. In an example embodiment with multiple distinct control circuits, a first control circuit controls a switching regulator that operates switch S1 in the charging circuit, whereas a second control circuit controls switches S2-S5 in the discharge portion of the circuit. These distinct control circuits can be distributed as depicted, there can be at least one closed-loop feedback arrangement, such as the measurement of the capacitor voltage Vcap, which the control unit uses to adjust the operation of the charging and discharging circuitry.

In operation, to deliver a biphasic defibrillation shock according to an exemplary embodiment, upon charging up of the capacitor to a suitable voltage for defibrillation, switches S2 and S5 are enabled for a period of time between 3 and 8 ms to deliver the positive phase to the chest (or directly to the heart in the case of an implantable device). Immediately afterwards, switches S2 and S5 are turned off by the control unit and switches S3 and S4 are enabled to a deliver a negative phase for approximately 3-4 ms.

For the delivery of a MVT pulse train according to an exemplary embodiment, switches S2 and S5 are turned on briefly to deliver a single pulse, then one or both of these switches is turned off. There is a delay until the start of the next individual pulse, then the next pulse is delivered in the same manner (i.e. conducting current through switches S2 and S5).

Figure 5A:
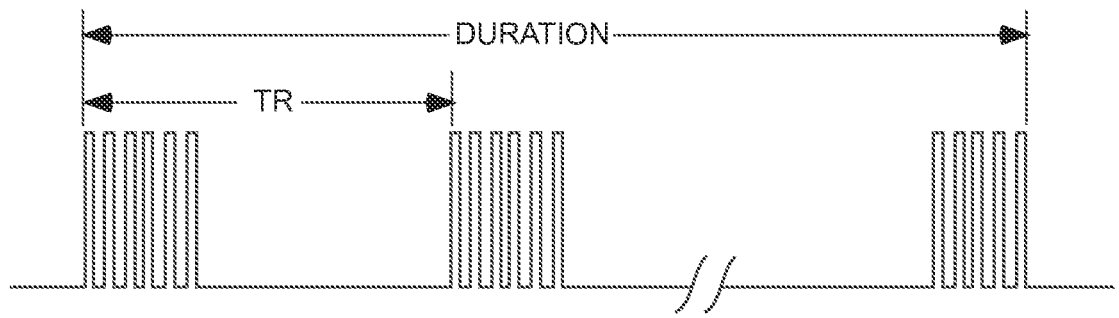
FIGS. 5A and 5B are waveform diagrams illustrating various conventional MVT parameters.
Figure 5B:
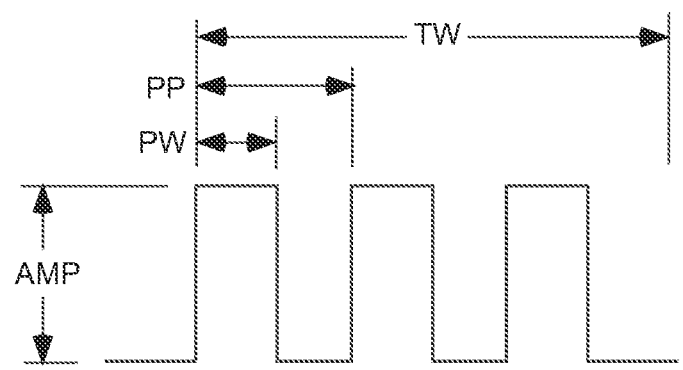

Conventional MVT waveforms are illustrated in FIGS. 5A and 5B. MVT therapy is composed of a plurality of pulse trains that are administered periodically for a treatment duration, as illustrated in FIG. 5A. The pulse trains are applied with a periodicity that can be expressed as a train rate TR. Pulse trains are composed of a predetermined number of individual pulses separated by an inter-pulse time duration. Each pulse train has a train width TW, as illustrated in FIG. 5B. The individual pulses inside the pulse train have a Pulse With PW. The pulses have a periodicity that can be expressed a pulse period PP.

For MVT, Table 1 below provides an exemplary range of parameter values corresponding to empirically determined effectiveness.

TABLE 1

Exemplary Parameter Value Ranges for MVT

| Parameter | Value of Parameter (Implanted Devices) | Value of Parameter (External Devices) |
| --- | --- | --- |
| MVT Duration | 5-120 s | 5-120 s |
| Train Rate | 30-160 per min. | 30-160 per min. |
| Pulse Current Amplitude | 0.25-5 A | 0.25-5 A |
| Pulse Voltage Amplitude | 15-250 V | 60-300 V |
| Pulse Width | 0.15-10 ms | 0.15-10 ms |
| Pulse Period | 5-70 ms | 5-70 ms |

The MVT waveform can be further tuned to increase selectivity of muscle type in the application of the MVT. Muscle type selectivity permits more precise targeted treatment based on the patient's condition, and facilitates management of muscle fatigue to prolong the MVT treatment duration.

An MVT waveform that is optimized for skeletal muscle capture (OSC) according to one embodiment is adapted to force primarily skeletal muscle contractions. The OSC waveform is adapted to force a contraction and subsequent release of skeletal muscles in order to achieve perfusion of the heart and other vital organs, and can force some amount of ventilation.

An MVT waveform that is optimized for myocardial capture (OMC) according to a related embodiment is adapted to force cardiac muscle contractions. The OMC waveform is adapted to force contraction of primarily cardiac muscles in order to achieve some level of perfusion for the heart and other vital organs. Tables 2 and 3 below provide exemplary ranges for OMC and OSC MVT parameter values; whereas tables 4 and 5 that follow provide an exemplary optimal set of values for OMC and OSC waveforms, respectively.

TABLE 2

Exemplary Stimulation Waveform for OMC

| Variable Parameter | Optimal Range |
|---|---|
| Pulsed Output Voltage | 75-300 V (external); 20-80 V (implantable) |
| Pulsed Output Current | 1-5 A |
| Pulse Width | 5-10 ms |
| Pulse Period | 10-20 ms |
| Duration | 10-30 seconds |
| Packet Width | 100-300 ms |
| Train Rate | 80-160 bpm |

TABLE 3

Exemplary Stimulation Waveform for OSC

| Variable Parameter | Optimal Range |
|---|---|
| Pulsed Output Voltage | 75-300 V (external); 20-80 V (implantable) |
| Pulsed Output Current | 1-5 A |
| Pulse Width | 0.10-0.25 ms |
| Pulse Period | 20-40 ms |
| Duration | 10-30 seconds |
| Packet Width | 100-300 ms |
| Train Rate | 80-160 bpm |

TABLE 4

Exemplary Stimulation Waveform for OMC

| Variable Parameter | Optimal Value |
|---|---|
| Pulsed Output Voltage | 75-300 V (external); 20-80 V (implantable) |
| Pulsed Output Current | 2 A |
| Pulse Width | 7.5 ms |
| Pulse Period | 15 ms |
| Duration | 20 seconds |
| Packet Width | 200 ms |
| Train Rate | 120 bpm |

TABLE 5

Exemplary Stimulation Waveform for OSC

| Variable Parameter | Optimal Value |
|---|---|
| Pulsed Output Voltage | 75-300 V (external); 20-80 V (implantable) |
| Pulsed Output Current | 2 A |
| Pulse Width | 0.15 ms |
| Pulse Period | 30 ms |
| Duration | 20 seconds |
| Packet Width | 200 ms |
| Train Rate | 120 bpm |

Notably, in this conventional MVT waveform the width of the individual pulses in the pulse trains are constant, and the pulse amplitude for each of the individual pulses is generally constant. According to one aspect of the invention, as described above, the same charging, energy storage, and discharging circuit are used for the MVT as for the defibrillation therapy. In this type of electrotherapy, it is important to stimulate the patient with MVT just before applying defibrillation therapy. Stated another way, it is important to apply the defibrillation very soon after cessation of MVT. This presents a challenge in that it generally takes a considerable amount of time to charge the capacitors to a defibrillation-level voltage—on the order of 5-30 seconds or more for devices using efficient and practical charging circuits (e.g. 20-25 watt charging circuit for an external device and a 6-12 watt charging circuit for an implantable device charging to 360 J or 45 J for an implantable device). Notably, the charge times are longer than those suggested by a simple division of the energy by the charging power since the electrolytic capacitors have substantial leakage when their voltage approaches the maximum, i.e. a 20 watt charger will charge an external defibrillation capacitor to 40 J in 2 seconds (=40÷20). However, charging to the maximum 360 J requires more time than 18 seconds (=360÷20) due to this nonlinear leakage effect.

FIG. 6 illustrates how the capacitor energy increases with time according to an implementation in one type of embodiment. This example is based on a typical 22-watt charging circuit, which is typical for an external defibrillator, and a 200-joule delivered shock, which is also typical. An implantable cardioverter-defibrillator (ICD) has a charging circuit capable of typically 6-12 watts. Thus, in the case of an ICD, the shape of the capacitor charging energy would be the same but the final energy will be lower—on the order of 40 joules.

According to one aspect of the invention, the MVT waveform is adapted so that MVT according to certain embodiments described herein, which is therapeutically equivalent to the therapy provided by the conventional MVT waveform, is delivered from the energy storage capacitor while the capacitor is charging to a higher defibrillation therapy voltage. In a conventional defibrillator, the capacitor energy increases approximately linearly with time (due to increasing leakage in the capacitor, this curve is not completely linear, but that issue has no bearing here). In the plot of FIG. 6, for the embodiment represented, several small stair steps, or nibbles, are visible during the first 7.5 seconds. That is due to the fact that energy from the charging circuit is being used to deliver MVT to the patient. The nibbles are smaller at the beginning of the charging due to the fact that the MVT pulses are more energy efficient at the beginning while the nibbles get larger near the top as will be explained later. From 7.5 seconds on, there is no stepping in this embodiment as 100 percent of the charging energy is being devoted to "topping off" the main defibrillation shock capacitor.

According to one embodiment, MVT pulses are administered for a pulse width PW that produces a similar amount of charge transfer to the patient as a therapeutically similar conventional MVT waveform. In one embodiment, constant charge is maintained in the MVT pulses by adjusting the pulse width PW as the capacitor voltage changes. Thus, as the capacitor voltage increases due to charging, the pulse width is progressively reduced for successive pulses so that each pulse delivers approximately as much charge to the patient.

FIG. 7 illustrates the timing of the MVT pulse trains while the main capacitor undergoes charging according to one example embodiment. In the example illustrated here, the MVT is applied for a period of 60-120 seconds before the defibrillation shock is given. The chart in FIG. 7 is a chart that illustrates a portion of this period. In the chart, the time range prior to time 0 represents a period in which the capacitor is already charged up to an initial MVT-level voltage that is insufficient to defibrillate the heart but sufficient to administer MVT. This voltage during the first period is held for some time until the device determines that it is time for the capacitor to be charged further to prepare for administering defibrillation therapy. During this first period, the voltage on the capacitor is not changing appreciably, so MVT can be applied in conventional fashion.

After time 0 as shown in FIG. 7, the MVT pulse trains are delivered for a second period of time while the capacitor charges to the level called for to defibrillate the heart. This period of time can last from between several seconds to several tens of seconds, depending on the time required to charge the capacitor for defibrillation. Notably, the ability to deliver MVT during charging of the capacitor can allow the device to utilize a lower-wattage charging circuit, which may be particularly useful in implantable devices where size and energy conservation are particularly important design criteria. This is because administration of the MVT prior to defibrillation offers a benefit associated with delaying the administration of defibrillation; thus, the capacitor in a MVT-enabled device does not need to be charged for defibrillation as quickly as the capacitor of a device without MVT (or without the ability to administer MVT during charging of the capacitor for defibrillation).

Just prior to administration of the defibrillation shock, the MVT is ceased. Depending on the capabilities of the discharging circuit according to various embodiments, the time between cessation of MVT and administration of the defibrillation shock is between about 5 seconds and under one second. In one particular embodiment, this time period is about 3 seconds. This is a substantial advantage over other methods of delivering CPR, in that the gap between the end of the last chest compression and the delivery of the shock is on the order of only a few seconds. This is far smaller than the gap that is seen with manual chest compressions before the shock due to the operator fears of being of shocked and the timing requirements for pushing the defibrillator shock button.

FIG. 8 is a chart depicting the capacitor voltage in an embodiment that applies MVT during charging for defibrillation (note that this ignores the charge slowing at the peak voltage due to capacitor leakage). Since the energy in a capacitor is proportional to the voltage squared, the voltage curve is basically a square root function of the time. In this example, the curve is not a precise square root function since the voltage is precharged to 150 volts at time 0 before the capacitor begins to further charge in preparation to deliver defibrillation therapy. In this example, prior to time 0 the capacitor is maintained at 150 volts throughout the delivery of the MVT by running the charging circuit intermittently. When it is time to charge a capacitor up to its full voltage for the defibrillation shock, the capacitor has a small "head start" on the voltage since it is beginning at 150 V. Note that the stair steps stop at 7.5 seconds and the capacitor is of sufficient voltage to deliver its shock at about 10.5 or 11 seconds. In this embodiment, there is a short delay on the order of 3 seconds from the end of the MVT to the delivery of the defibrillation shock.

More generally, the voltage on the capacitor during charging while applying MVT according to one embodiment can be approximately represented mathematically as follows:

In short pulse range (d<50 μs) the required charge q is fairly constant. Also, assume constant charging power P. The following symbols are utilized in the expressions that follow:

E=capacitor energy
C=capacitance of capacitor
V=voltage on capacitor
R=resistance of shock path
t=time into charging cycle
f=train rate in pulses per second $$E = Pt$$

$$= \tfrac{1}{2}CV^2$$

$$V = (2Pt/C)^{1/2}$$

For constant charge:

$$q = Vd/R$$

hence, $$d = qR/V$$

for the pulse duration. Hence $$d = qR\sqrt{\frac{C}{2Pt}}.$$

Energy per pulse is then given by:

$$E = \frac{dV^2}{R}$$

$$= \left[\frac{qR}{V}\right]\left[\frac{2Pt}{C}\right]\left[\frac{1}{R}\right]$$

$$= 2qPt/C$$

Hence, the average power lost to the MVT nibbles is:

$$P' = Ef = 2fqPt/C.$$

Thus, the net power delivered to the capacitor is:

$$P - 2fqPt/C$$

The energy on the capacitor as a function of time is then given by:

$$E(T) = \int_0^T (P - 2fqPt/c)dt$$

$$E(T) = P[T - qfT^2/C]$$

Since $E = \tfrac{1}{2} CV^2$, we have $$V = \sqrt{\frac{2P(T - qfT^2)/C}{C}}$$

$$V = \sqrt{\frac{2P(TC - qfT)}{C^2}}$$

$$V = \frac{\sqrt{2PT}}{C}\sqrt{C - qfT}.$$

This can be separated into 2 terms by squaring V:

$$V^2 = \frac{2PT}{C^2}[C - qfT]$$

giving:
$$V^2 = \frac{2PT}{C} - \frac{2PT^2 qf}{C^2}$$

and, finally:

$$V = \left(\frac{2PT}{C} - \frac{2PT^2 qf}{C^2}\right)^{\frac{1}{2}},$$

where the left-most term represents conventional capacitor charging without the extraction of the MVT nibble energy and the term right-most term represents that extraction.

FIG. 9 is a chart depicting the MVT pulse duration for OSC pulses as a function of time for an embodiment in which successive pulses are progressively narrowed as the capacitor voltage is increased during charging. This is given by the following equations:

$$I = I_r(1 + d_c/d)$$

(from classical strength-duration theory).
A rheobase current ($I_r$) of about 1 ampere is sufficient to produce good cardiac output with external patches. Assuming a skeletal muscle stimulation chronaxie value of $d_c = 150$ µs this gives a required current of:

$$2A = I_r(1 + 150 \text{ µs}/150 \text{ µs})$$

for a 150 µs pulse in this example.
In general (assuming the typical 1 A rheobase)

$$I = (1 + d_c/d)$$

$$dI = d + d_c$$

$$d(I - 1) = d_c = 150 \text{ µs}$$

Since I=V/R, we have:

$$d = \frac{150 \text{ µs}}{V/R - 1}$$

Since the metric of stimulation capability of a pulse is the charge, the pulse duration d is approximately inversely proportional to the voltage that is applied. Thus, as the capacitor voltage is increased during the charging time from 0 to 7.5 seconds in this example, the pulse duration is varied from about 45 µs down to about 10 µs. This gives a constant charge of approximately 300 microcoulombs. At the end of the 7.5 seconds, no pulses are delivered and the main shock capacitor is merely being topped off for the shock.

FIG. 10 is a chart illustrating the energy cost of delivering the stimulation charge by using narrow pulses of higher voltage according to one embodiment. Even though the charge applied to the patient with each pulse is kept constant by keeping the pulse duration d inversely proportional to the voltage, the energy is not constant.

$$d = \frac{150 \text{ µs}}{V/R - 1}$$

$$\sim \frac{150 \text{ µs}}{V/R}$$

$$\text{Energy} = dV^2/R$$
$$= [150 \text{ µs} * R/V]V^2/R$$
$$= 150 \text{ µs} * V$$

The energy per pulse increases with the voltage and thus the energy in each pulse train increases from less than 0.4 joules up to almost 2.0 joules by the time the electrical CPR is terminated at 7.5 seconds in the example quantified here. This energy cost slightly interferes with the charging of the main capacitor and is what causes the small stair steps in FIGS. 6 and 8. However, it is not sufficient to halt the charging of the capacitor since, even at the maximum energy loss at 7.5 seconds, the medium voltage therapy is never more than 10% of the typical 22-watt charging ability of the exemplary charging circuitry for external devices (or 12 watts for a typical ICD).

In this example, the total cost in terms of charge time with the addition of MVT is less than one additional second. Moreover, this cost is far outweighed by the benefits of MVT.

FIG. 11 is a chart illustrating the net charging energy per 0.1 second (100 ms) period according to one embodiment. Since the charging circuit in the exemplary external device embodiment is capable of delivering 22 watts, it delivers an energy of 2.2 joules per 100 ms time period. Even at the maximum MVT energy requirement of almost 2 joules per pulse train, at 7.5 seconds, there is still sufficient energy being delivered to the capacitor to charge it in full in this example.

In another approach to solving the problem of delivering MVT while charging the capacitor for defibrillation therapy, the delivery circuit includes a provision for stepping down the higher voltage stored in the capacitor to a voltage suitable for MVT. In this approach, a switching regulator such as a buck regulator is employed to produce a reduced voltage at the top of the H-bridge circuit. This approach essentially chops each individual MVT pulse into a plurality of even narrower pulses that have varying pulse widths. This pulse width modulated (PWM) power signal is then filtered so that its average value so that its spectral content applied to the patient is similar to that of conventional MVT pulses.

Figure 12:
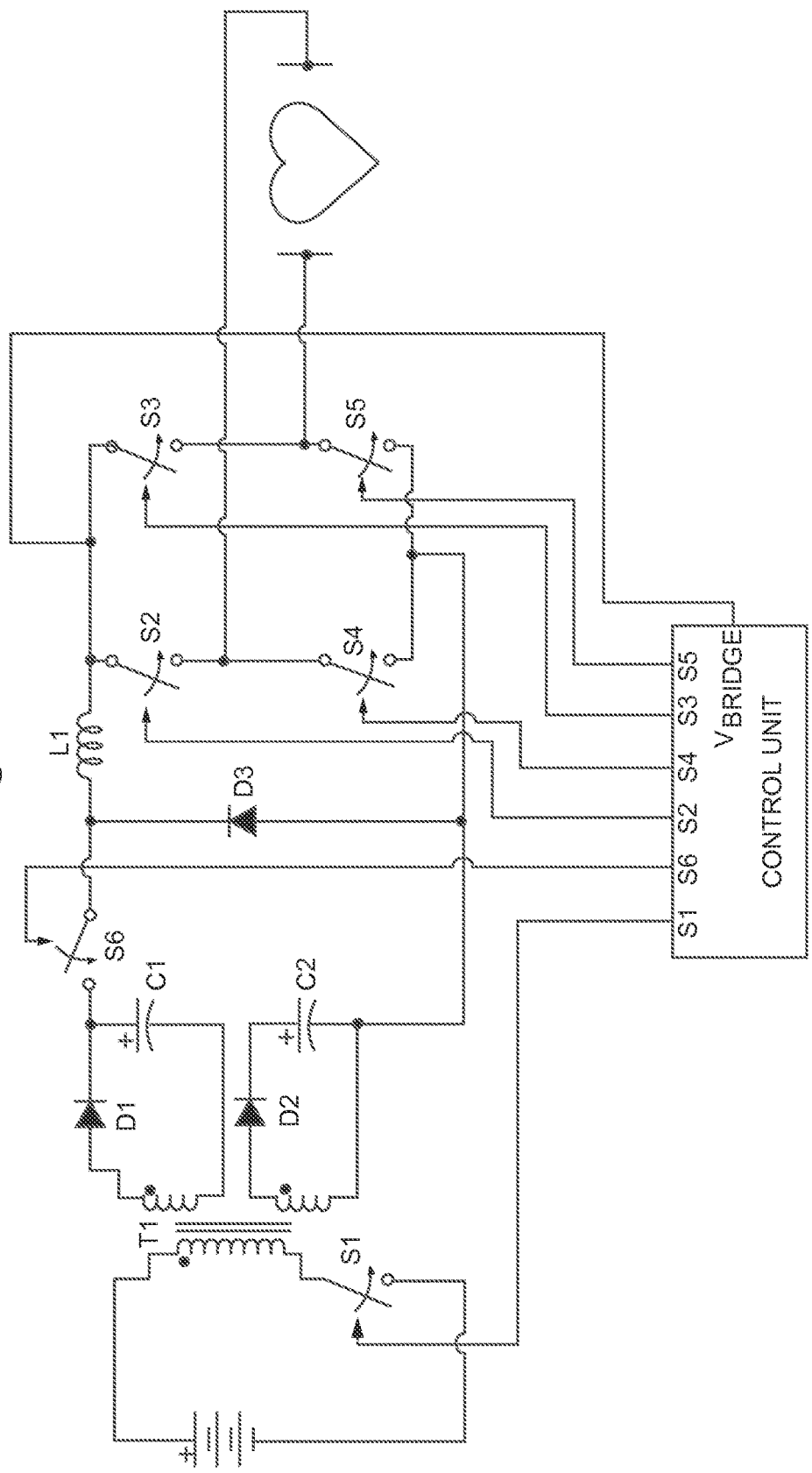
FIG. 12 is a simplified schematic diagram illustrating modifications that can be made to the circuit of FIG. 4 to accommodate a switching regulator according to one example embodiment.

FIG. 12 is a simplified schematic diagram illustrating modifications that can be made to the circuit of FIG. 4 to accommodate a switching regulator according to one example embodiment. In this embodiment, the added components include switch S6, inductor L1, and diode D3. The control unit controls switch S6 in a rapid switching mode that using pulse width modulation (PWM) based on voltage feedback signal $V_{bridge}$. Inductor L1 integrates the switched power signal to provide a substantially constant voltage at the top of the H-bridge. The value of inductor L1 is such that it is inconsequential to the MVT pulse attributes, though it will tend to slow the rise and fall times of the pulses by some small amount, which may even be a desired result in some cases. Diode D3 provides a current return path for the part of the switching cycle of switch S6 when the switch is open. This smoothing of the currents can provide an additional benefit for defibrillation therapy since the high initial peak current is somewhat damaging to the heart and does not provide help with defibrillation.)

In a related embodiment, the control unit is configured such that, at the conclusion of each MVT pulse (composed of a PWM signal), switch S6 is opened to stop the flow of current from the capacitors before the H-bridge switches are opened. In this regime, the H-bridge switches delivering the MVT current to the patient (e.g., S2-S5, or S3-S4) remain closed for a short time period that is sufficient to allow the energy magnetically stored in inductor L1 to dissipate. This prevents inductor L1 from developing a voltage spike due to the collapse of the magnetic field in L1 if the current through the inductor were suddenly interrupted. In a related embodiment, shoot-through is utilized to internally dissipate the energy stored in inductor L1 by shorting a single leg of the H-bridge (e.g., S2-S4) upon opening of switch S6.

Figure 13:
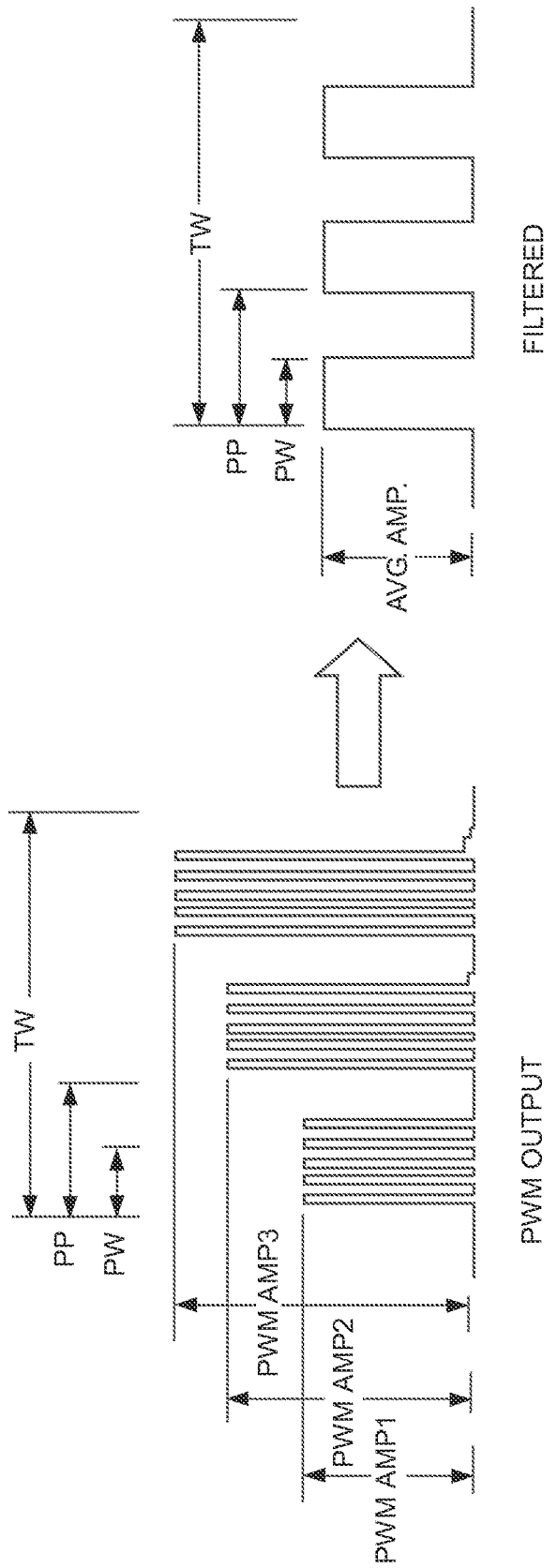
FIG. 13 is a diagram illustrating the general operation of the PWM circuitry of FIG. 12 for generating controlled-amplitude individual MVT pulses according to one embodiment.

FIG. 13 is a diagram illustrating the general operation of the PWM circuitry of FIG. 12 for generating controlled-amplitude individual MVT pulses according to one embodiment. The PWM output on the left-hand side of FIG. 13 represents the voltage at the cathode of D3. Note that the voltage waveform is not drawn to scale in this schematic diagram. As depicted, successive MVT pulses are generated as the capacitor voltage increases due to charging of the capacitor. These peak voltages are indicated as PWM Amp1, PWM Amp2, and PWM Amp 3. Switch S6 switches the capacitor in and out of the circuit to produce a switched voltage. The duty cycle of this switching produces an average voltage that is the same for successive individual MVT pulses. Thus, for an increasing capacitor voltage, the duty cycle is reduced. The inductor L1 filters the peaks and valleys of the switched waveform to produce a steady (non-switched) average voltage with none to negligible ripple. The filtering may be accomplished with a more elaborate filtering network using one or more additional filtering capacitors or inductors in other embodiments. The filtered waveform is depicted on the right-hand side. Each individual MVT pulse has the same pulse amplitude equal to Avg. Amp. The pulse width PW, pulse period PP, and train width TW are substantially unaffected.

In a related embodiment, the variable pulse width technique of transferring a common amount of charge to the patient with each pulse is used in conjunction with the PWM technique of adjusting the average pulse amplitude for each individual pulse to achieve greater control of the MVT pulse current and duration.

Figure 14A:
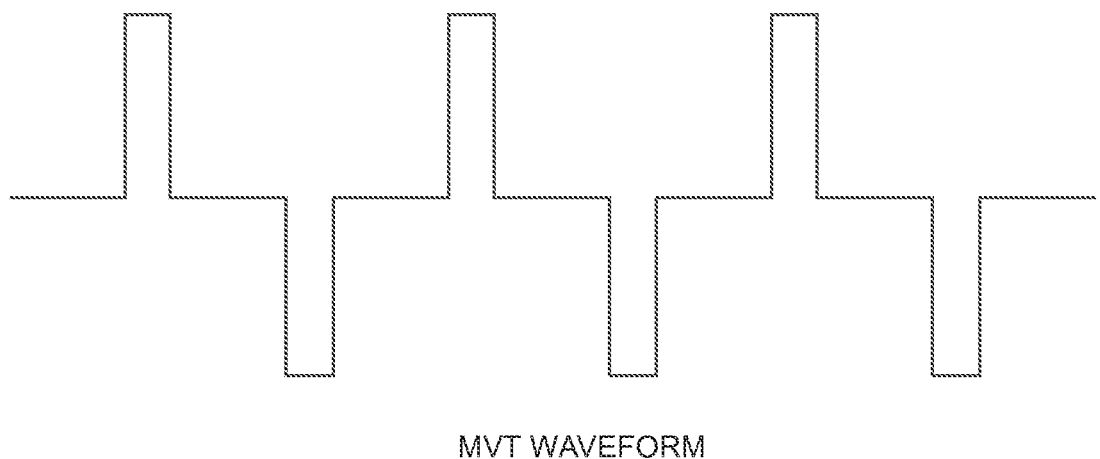
FIGS. 14A-14B are diagrams illustrating exemplary MVT waveforms according to another aspect of the invention.
Figure 14B:
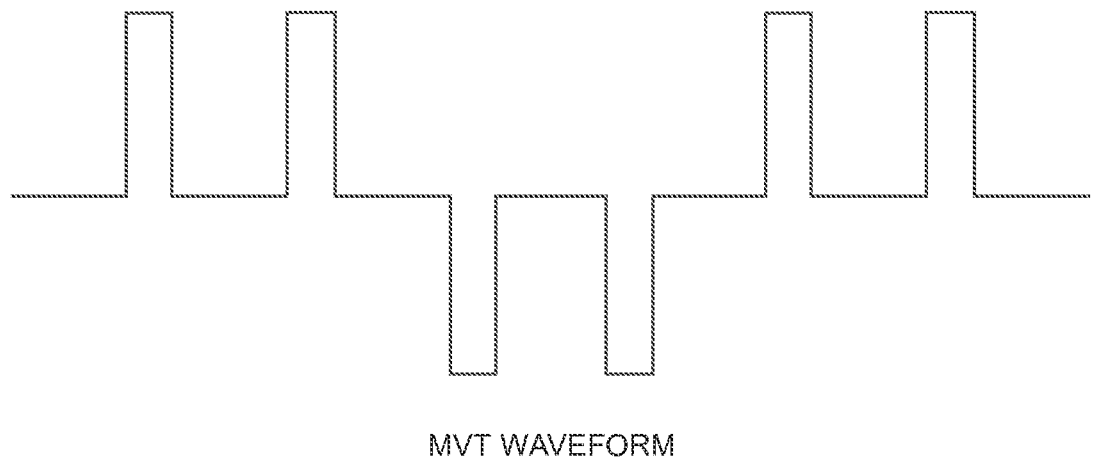

FIGS. 14A-14B are diagrams illustrating exemplary MVT waveforms according to another aspect of the invention. As depicted, the MVT waveform includes pulses in both polarities. The benefit of this technique is based on the recognition that muscle is stimulated far more efficiently with a negative or "cathodal" pulse. Thus, more muscle tissue near the negative electrode will be stimulated than the muscle tissue near the positive electrode. Thus, by alternating the polarity, embodiments of this invention capture more total muscle mass, and more widely distributed muscle mass. In addition, the captured muscle mass, as a whole, experiences less fatigue by virtue of having certain portions that are less frequently stimulated. These portions are muscle tissue that is captured when the MVT is applied in one polarity but not the other.

In the embodiment of FIG. 14A, each successive individual MVT pulse is of an alternating polarity. In the embodiment of FIG. 14B, the polarity changes for every two pulses. In other embodiments, the polarity can changed for every $n^{th}$ pulse, for example. In general, it is beneficial for the polarity of the MVT to be alternated relatively frequently, though in related embodiments, the polarity is alternated between successive pulse trains, or every $m^{th}$ pulse train. Also, it is generally preferable for the alternating polarity to be approximately evenly distributed between positive and negative pulses, though it does not have to be exactly evenly balanced.

The alternating polarity MVT pulses can be supplied using the H-bridge circuitry discussed above with reference to FIGS. 4 and 12 by alternating the current flow through switches S2-S5 and S3-S4.

Figure 15:
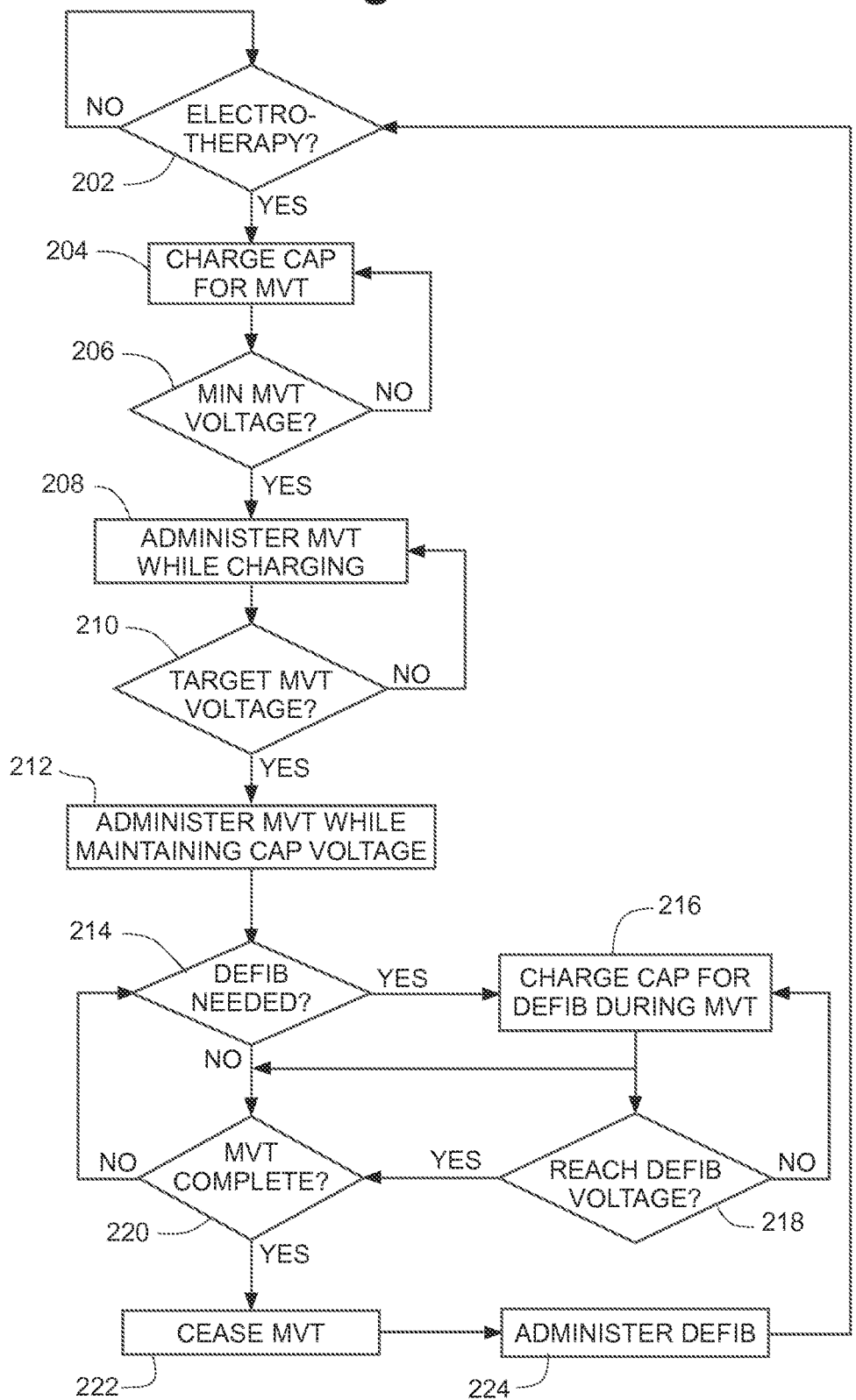
FIG. 15 is a flow diagram illustrating a basic operational algorithm for an electrotherapy device according to one embodiment.

FIG. 15 is a flow diagram illustrating a basic operational algorithm for an electrotherapy device according to one embodiment. In this electrotherapy device, the charging circuit and energy storage capacitor is shared for MVT and defibrillation therapies. At 202, the controller of the device checks the patient and determines a need for electrotherapy, MVT, defibrillation, or both. If electrotherapy is called for, at 204 the controller operates the charging circuit to begin charging the capacitor for MVT. At 206 a check is made if the minimum voltage for MVT is reached, at which point the MVT can be started at 208, while the capacitor continues charging. To apply MVT during charging, one or more techniques described above are employed to maintain an approximately constant charge transfer to the patient in each MVT pulse. At 210, a determination is made if the target MVT voltage is reached in the capacitor. This is a voltage at which the MVT can be applied most efficiently with the best effectiveness. In the examples provided above, this voltage is on the order of 150 volts for an external device, though other target voltages can certainly be used as appropriate. Until the target voltage is reached, the capacitor continues to be charge during MVT administration. Once reached, the target voltage can be maintained for some period of time to apply MVT at 212 for a prescribed time duration (or as needed based on continued patient monitoring).

At 214, a determination may be made as to whether defibrillation is needed. This is because the MVT might have facilitated a spontaneous conversion of the patient's arrhythmia although this is not the primary objective of the MVT. If defibrillation is called for, the capacitor is further charged up at 216 to the prescribed defibrillation voltage. At 218 a check is made to either continue charging or proceed. During this time, MVT can be continued according to one type of embodiment.

At 220, a check is made whether MVT should be concluded. This inquiry can occur during or after each check of the capacitor voltage during charging, as shown in FIG. 15. The need to conclude MVT may arise from the prescribed time for applying defibrillation being reached according to the device's rescue algorithm parameters. Otherwise, the MVT may be continued in some embodiments, even upon reaching of the defibrillation voltage. When it is time to apply the defibrillation, 222, MVT is ceased, and the defibrillation shock is applied at 224. The defibrillation shock is preferably applied very soon after cessation of the MVT, such as within 5 seconds, 3 seconds, 1, second, etc., depending on the capabilities of the discharge circuitry and on the rescue protocol of the electrotherapy device. The patient is then checked, and the process repeated if necessary.

More information about the above described embodiments for delivery MVT and defibrillation therapy pulses can be found in U.S. patent application Ser. No. 13/567,699, filed Aug. 6, 2012, the disclosure of which is incorporated herein by reference (except for the claims, summary of the invention, and any express definitions).

Figure 16:
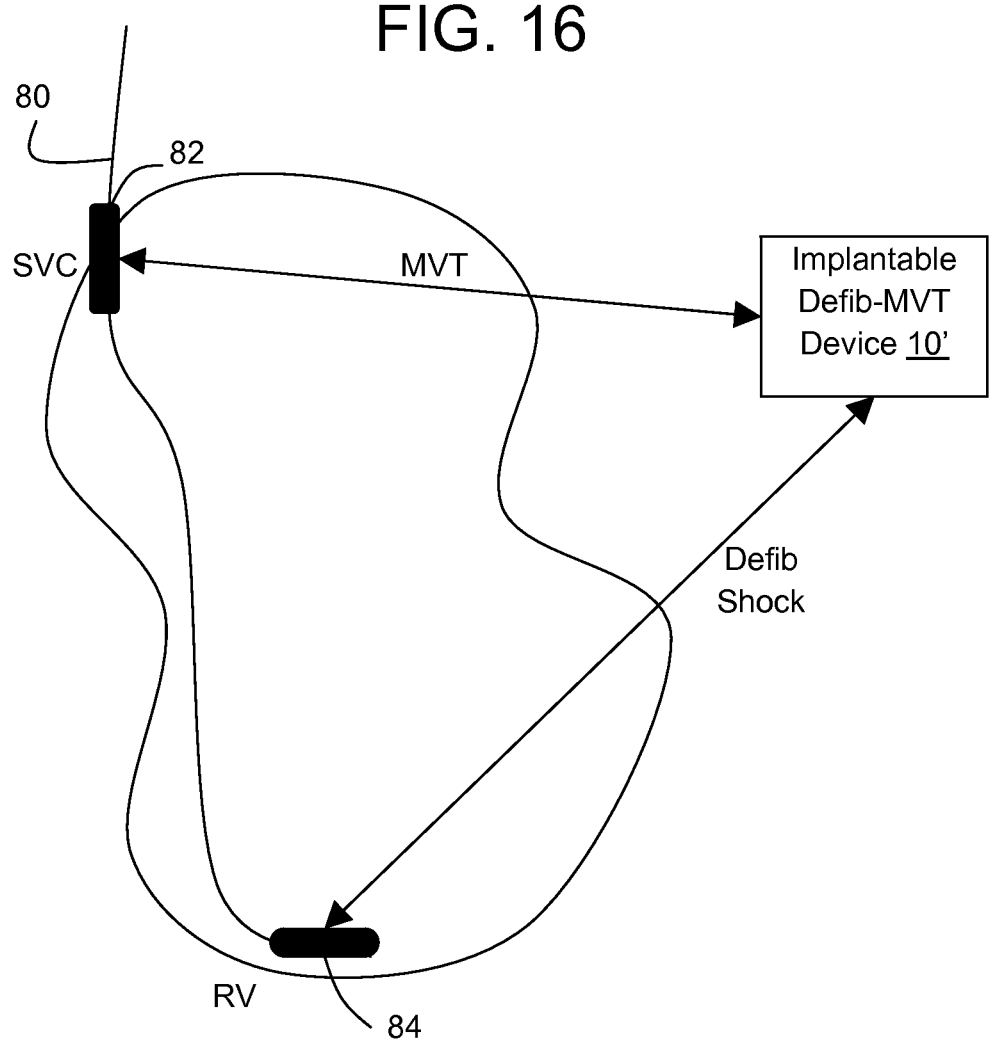
FIG. 16 is a schematic diagram illustrating the use of differing vectors for delivering MVT and defibrillation therapy.

FIG. 16 is a diagram depicting various electrotherapy application vectors according to certain embodiments of the invention. In this example, the implantable device (IMD) 10' is operably coupled to a endocardial lead 80 having coil electrodes 82, 84 implanted such that SVC coil electrode 82 is in electrical contact with the superior vena cava (SVC) and RV coil electrode 84 is in electrical contact with the right ventricle (RV). In this configuration, electrotherapy can be delivered across multiple vectors by directing current between the implantable device 10' and SVC coil electrode 82, the implantable device 10' and RV coil electrode 84, or SVC coil electrode 82 and RV coil electrode 84. In one example embodiment, MVT therapy can be directed to vectors not involving the ventricles (for example, by directing current between the implantable medical device 10' and the SVC coil electrode 82). Similarly, defibrillation therapy can be directed to vectors that do involve the ventricles. According to one embodiment, a primary function of MVT to treat or prevent PEA is to generate muscle contractions to give supportive cardiac output via chest compressions. This is accomplished according to one approach via SVC coil electrode 82 in the SVC region so that the MVT current is minimal in the ventricles in order to reduce the risk of inducing VF. While an implantable device and electrodes are depicted in FIG. 16, it is appreciated that an another embodiment can include an external combined MVT-defibrillation device with externally applied cutaneous electrode pads configured as known in the art to direct current along vectors which include or avoid the ventricles as appropriate. For example a electrode pad placed above the sternum of the chest can approximate an electrode directly in contact with the RV.

Other vectors involving the right atrium (RA) and left ventricle (LV) can also be utilized. Table 6 below further illustrates various electrotherapy application vectors that can be selected according to various embodiments. Notably, in these embodiments, no electrotherapy application vector is used for both, defibrillation therapy, and MVT.

TABLE 6

Exemplary Therapy Vectors

| Vector | Used for MVT? | Used for Defibrillation? |
|---|---|---|
| SVC↔IMD | Yes | No |
| SVC↔RV | No | Yes |
| SVC↔LV | No | Yes |
| SVC↔RA | Yes | No |
| IMD↔RV | No | Yes |
| IMD↔LV | No | Yes |
| IMD↔RA | Yes | No |
| RV↔LV | No | Yes |
| RV↔RA | No | Yes |
| LV↔RA | No | Yes |

Figure 17:
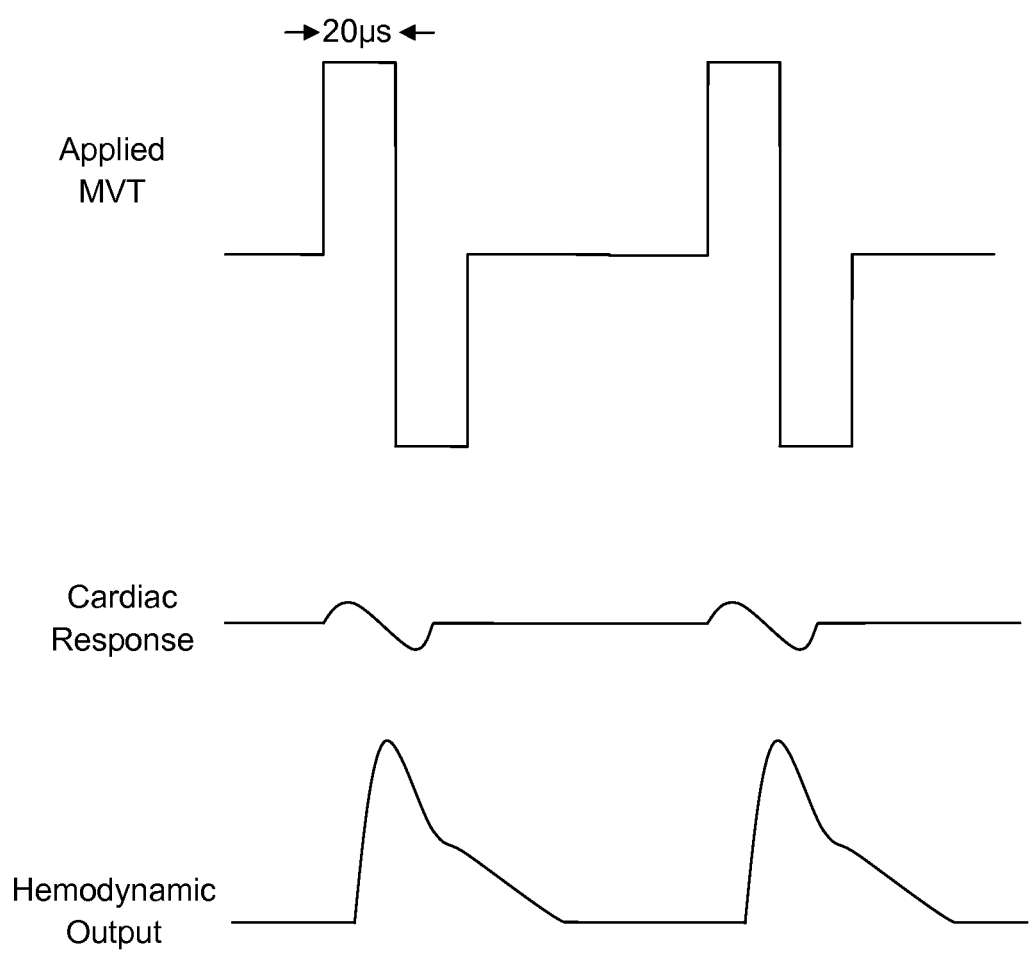
FIG. 17 is a diagram illustrating an exemplary MVT waveform with short biphasic shape that captures motor neurons but not cardiac cells according to one embodiment.

FIG. 17 depicts sample MVT waveforms with short biphasic shapes (e.g., phases of 10-50 us in duration). According to one embodiment, the implantable medical device can generate MVT pulses with biphasic waveforms of short duration (phases of 10-50 μs), and sufficient amplitude to cause capture of the skeletal muscles. The short biphasic pulses stimulate alpha motor neurons which causes the capture of the skeletal muscles. However, such short biphasic pulses are ineffective to stimulate the cardiac cells, which have longer (i.e., slower) time constants. However, the skeletal muscle capture can cause chest constrictions that result in oxygenated blood delivery to the heart muscles. Because the cardiac cells are not captured by the short biphasic pulse, they will not be in refractory state and may be able to respond more productively to further antitachycardia/defibrillation therapy or a spontaneous return to normal sinus rhythm. An illustration of two short biphasic pulses according to an example embodiment is given in the top curve labeled Applied MVT. The response of the cardiac cells is illustrated in the middle trace labeled Cardiac Response. The bottom trace, labeled Hemodynamic Output, illustrates the hemodynamic output produced by applying the short biphasic pulses that are effective for stimulating the alpha motor neurons that cause skeletal musculature to contract and thereby compress the heart momentarily. The pulse shaping circuitry adapted to generate the biphasic pulses can be incorporated into the output circuitry 26 of FIG. 1.

Figure 18:
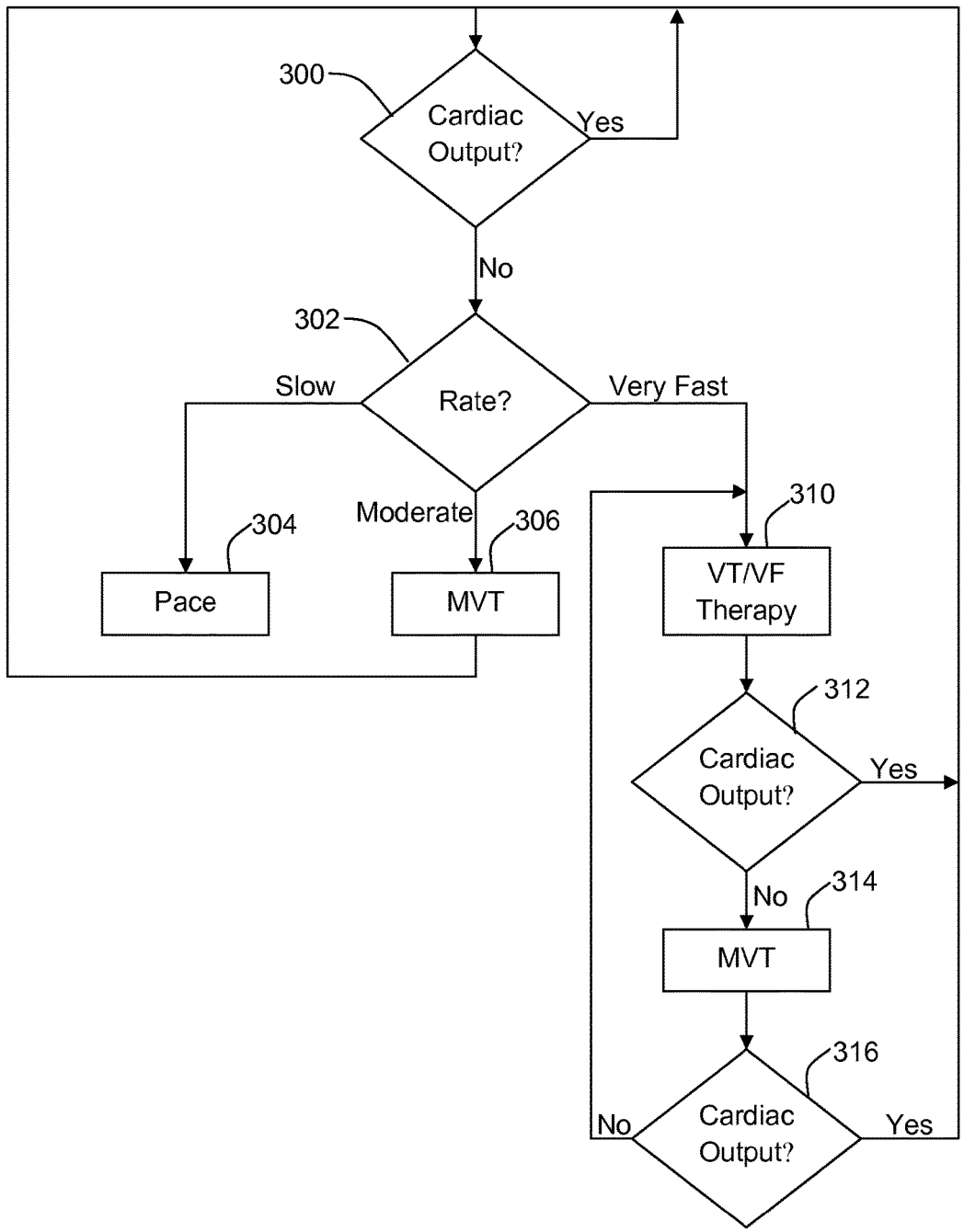
FIG. 18 is a flow diagram illustrating an operational algorithm which involves confirming a loss of cardiac output with a hemodynamic sensor according to one embodiment.

FIG. 18 is a flow diagram depicting an operational algorithm implemented in a controller of an electrotherapy device that determines when to apply MVT and/or conventional VT/VF therapy according to one embodiment. The electrotherapy device can be implantable or external to the patient. According to this embodiment, a hemodynamic sensor (as described above in reference to FIG. 1) operates to detect a loss of cardiac output at decision 300. When loss of cardiac output is detected, the device can select an appropriate therapy based on the current heart rate determined at decision 302. If the rate is slow, for example, less than or equal to about 30 BPM, the device can apply pacing therapy at 304. If the rate is moderate, for example, greater than about 30 BPM but less than or equal to about 200 BPM, PEA can be assumed to be the prevailing condition of the patient, and in response, MVT therapy is applied immediately at block 306. The duration of MVT 306 can be about 30 seconds. If the rate is very fast, for example, greater than about 200 BPM, the device recognizes a VT/VF arrhythmia and in response applies conventional VT/VF therapy at 310 (for example in the form of antitachycardia pacing or a defibrillation shock). Cardiac output is again monitored at 312. If cardiac output is still not found, MVT is applied at 314. The duration of MVT 314 can be about 20 seconds. If cardiac output is still not detected at decision 316, the device can attempt conventional VT/VF therapy again at 310. The rate ranges for each zone (slow, moderate, fast) can be predefined and configured in the controller based on an initial configuration definition, or selectably configured by a clinician. This example further improves the risk-benefit tradeoff of MVT for the treatment of VF because MVT is less likely to be applied without proper indication. In addition, by confirming PEA before applying MVT, the risk of delivering painful therapy to a conscious patient is reduced.

Figure 19:
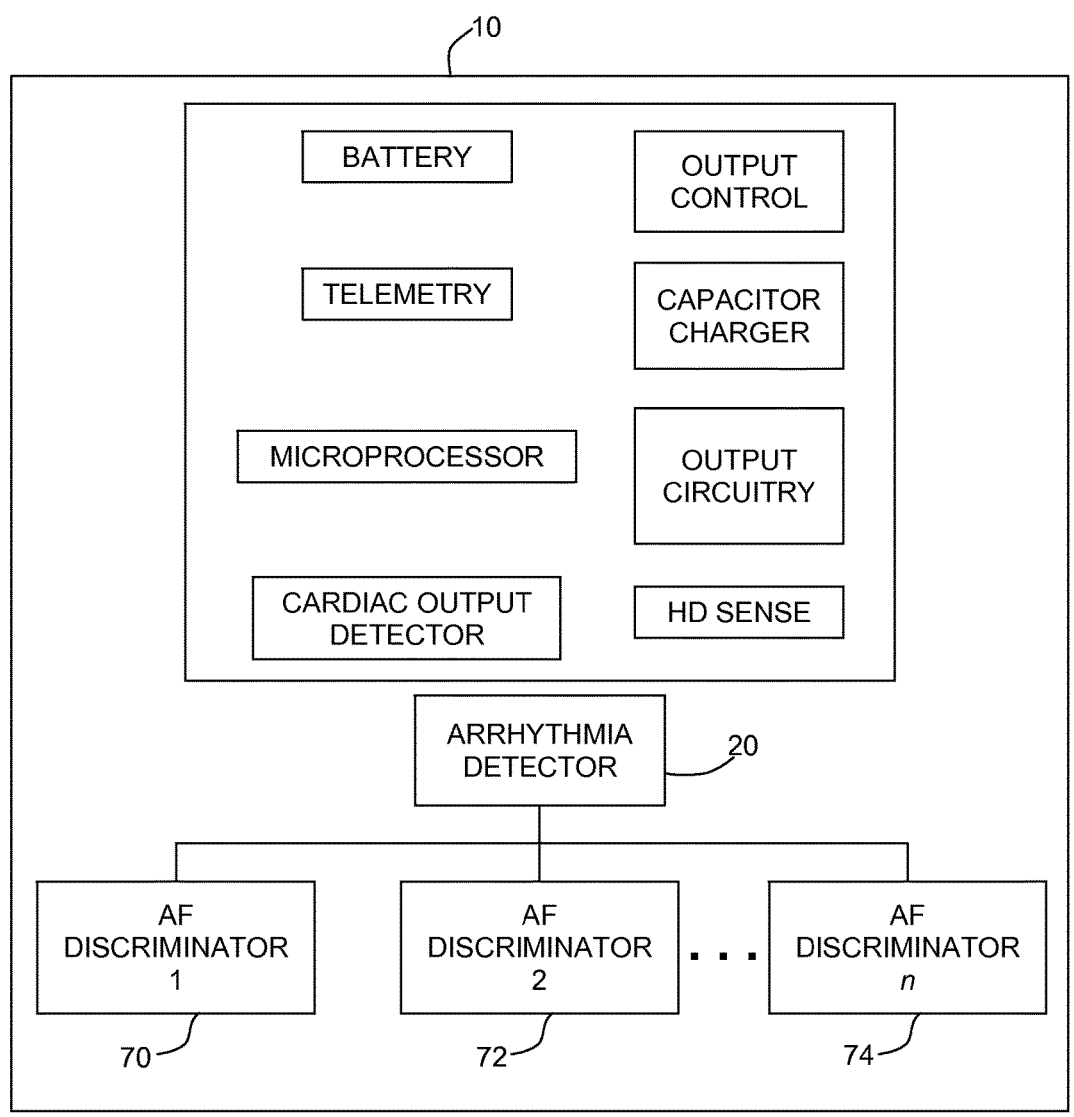
FIG. 19 is a block diagram illustrating an embodiment of a implantable medical device that includes one or more atrial fibrillation (AF) discriminators.

FIG. 19 is a block diagram illustrating an implantable electrotherapy device 10 according to one embodiment that includes one or more fibrillation discriminators 70, 72, 74. The fibrillation discriminators 70, 72, 74 can be any type or combination of sensors and detection algorithms useful for determining whether an arrhythmia is atrial fibrillation (AF) or VF. Some fibrillation discriminators known in the art include morphology sensors, atrial-ventricular (AV) synchrony detection, atrial chamber AF detection, and VF detection delay. While an implantable device and is depicted in FIG. 19, it is appreciated that another embodiment can include an external combined MVT-defibrillation device.

Figure 20:
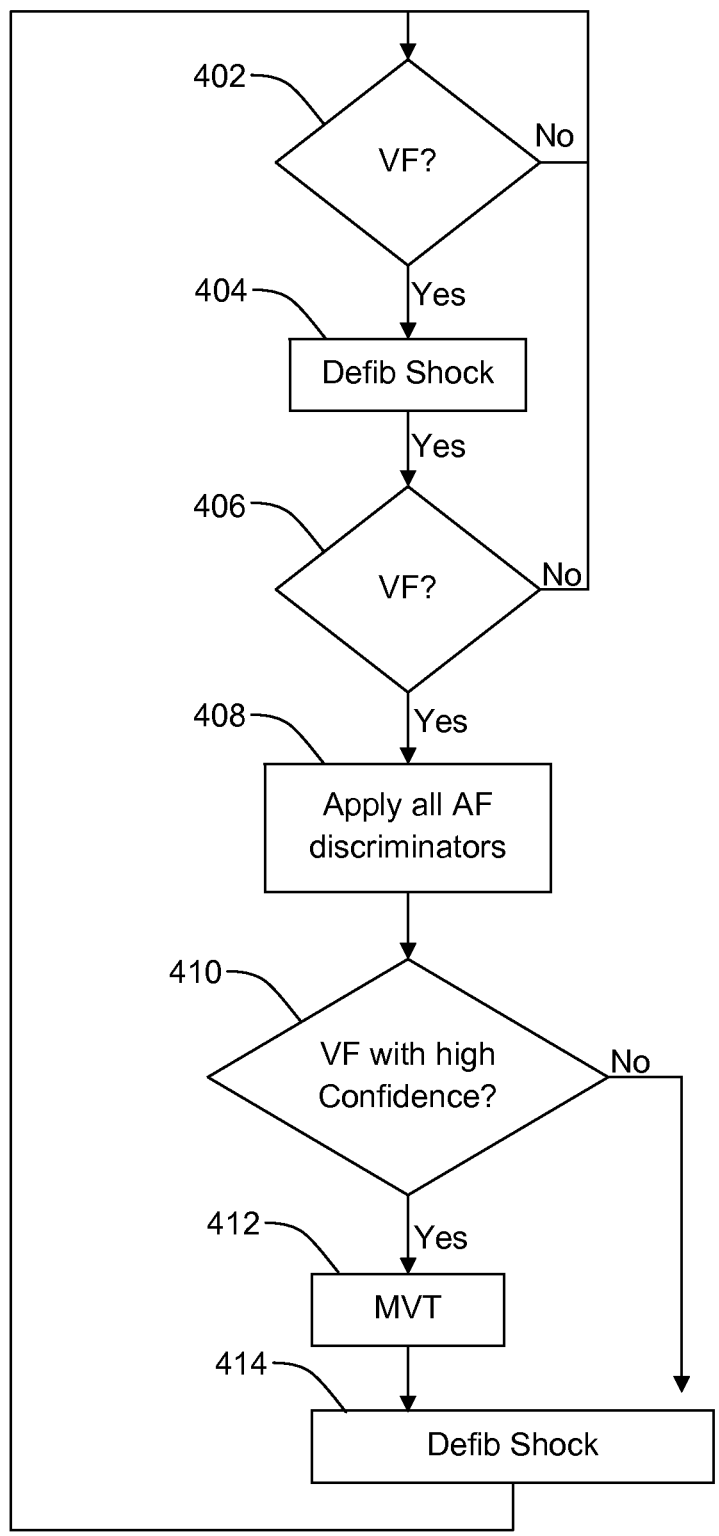
FIG. 20 is a flow diagram illustrating an operation algorithm which involves using a higher level of AF discrimination than that used normally for the detection of VF and restricting MVT to usage only after the 1st VF shock according to one embodiment.

FIG. 20 depicts an operational algorithm for therapy selection using a higher level of AF/VF discrimination than that used normally for the detection of VF and restricting MVT to usage only after the 1st VF shock. When VF is detected 402, the device can apply conventional VF therapy such as a defibrillation shock 404. If VF is still detected 406, a higher level of AF/VF discrimination can be applied 408. For example, the device can use all or most of the fibrillation discriminators available in order to determine with very high confidence that the current arrhythmia is VF. If there is a high confidence of VF 410, MVT can be applied 412 before the application of another defibrillation shock 414. The duration of application of MVT 412 can be about 15 seconds, or other time period as appropriate to provide therapy. If there is not a high confidence of VF 410, MVT can be suppressed and another defibrillation shock 414 or other VF/VT therapy can be applied. By increasing the required confidence levels (of the fibrillation discriminators) and applying more or all of these discriminators, the risk of falsely detecting VF falls to near zero. What we teach here is the novel idea of using a different level of discrimination for the VF shock only and for the MVT which can improve patient outcomes by reducing the risk of providing inappropriate or painful therapy.

In an example embodiment, the device could be capable of AV synchrony detection as well as AF detection by sensing in the atrial chamber. Each discriminator can be configured with thresholds for high or low confidence of VF. For example, AV synchrony detector could be configured to report that there is a high confidence of VF if there is a large (greater than 50%) dyssynchrony between the RA and the RV. Similarly, the AF detector can be configured to report a high confidence of VF if the atrial rate is normal (for example, between 30 and 200 BPM). The device can be configured to report a high confidence of VF if both of the discriminators report a high confidence, and a low confidence if one or both of the discriminators does not report a high confidence. The confidence levels can be predefined and configured in the controller based on an initial configuration definition, or selectably configured by a clinician.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the spirit and scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. An electrotherapy apparatus adapted for applying therapy for treating a patient experiencing an arrhythmia, the apparatus comprising:
    a power source adapted to supply energy for operation of the apparatus;
    electrotherapy administration circuitry electrically coupled to the power source and to a set of patient terminals, and constructed to generate electrotherapy pulses using the energy from the power source and apply a series of the electrotherapy pulses via the patient terminals in response to a control signal, the electrotherapy pulses comprising defibrillation pulses having energy and waveform characteristics sufficient to shock the heart of the patient into a reset state, and medium voltage therapy (MVT) pulses having an insufficient energy level to shock the heart into a reset state, but having an energy level and waveform characteristics that cause targeted musculature in the patient to be electrically activated into a contracted state, electrically maintained in the contracted state for a compression duration, and thereafter allowed to relax, thereby achieving a forced compression and release of that targeted musculature;
    monitoring circuitry electrically coupled with the power source and the set of patient terminals, and constructed to monitor the patient for indicia of the arrhythmia;
    controller circuitry electrically coupled with the power source, the electrotherapy administration circuitry, and the monitoring circuitry, the controller circuitry including a processor and a data storage device containing instructions that, when executed by the processor, cause the controller circuitry to read an output of the monitoring circuitry and determine any presence of the arrhythmia based on that output, and to generate the control signal causing the electrotherapy administration circuitry to apply the series of electrotherapy pulses;
    wherein the electrotherapy administration circuitry includes a therapy selection circuit constructed to cause the electrotherapy administration circuitry to deliver the defibrillation pulses to a first electrotherapy vector that includes at least one electrode in the right ventricle of the patient's heart and the MVT pulses to a second electrotherapy vector that omits electrodes in the right ventricle.

2. The electrotherapy apparatus of claim 1, wherein the monitoring circuitry further comprises a plurality of fibrillation discriminators, each adapted to distinguish between atrial fibrillation and ventricular fibrillation, wherein the plurality of fibrillation discriminators are operated collectively to provide a higher confidence level of detected fibrillation type relative to any one of the plurality of fibrillation discriminators operating individually.

3. The electrotherapy apparatus of claim 2, wherein the monitoring circuitry is adapted to report detection of ventricular fibrillation when one or more of the plurality of fibrillation discriminators report detection of ventricular fibrillation.

4. The electrotherapy apparatus of claim 3, wherein the monitoring circuitry is adapted to report detection of ventricular fibrillation when a majority of the plurality of the fibrillation discriminators report detection of ventricular fibrillation.

5. The electrotherapy apparatus of claim 1, wherein the second electrotherapy vector comprises at least one electrode in the superior vena cava of the patient.

6. The electrotherapy apparatus of claim 1, wherein the electrotherapy administration circuitry further comprises a pulse shaping circuit adapted to generate a biphasic waveform that includes a first phase and a second phase, wherein the first phase is less than 50 microseconds in duration.

7. The electrotherapy apparatus of claim 1, further comprising:
- a hemodynamic sensor, operably coupled to the therapy selection circuit and adapted to detect a presence of cardiac output; and
- wherein the therapy selection circuit is further adapted to withhold MVT pulses when the hemodynamic sensor detects the presence of cardiac output.

8. The electrotherapy apparatus of claim 7, wherein the therapy selection circuit is further adapted to provide NWT pulses when the hemodynamic sensor does not detect the presence of cardiac output and the heart rate is within a normal range.

* * * * *

UNITED STATES PATENT AND TRADEMARK OFFICE
CERTIFICATE OF CORRECTION

PATENT NO. : 9,713,727 B2  
APPLICATION NO. : 14/228694  
DATED : July 25, 2017  
INVENTOR(S) : Mark W. Kroll Page 1 of 1

It is certified that error appears in the above-identified patent and that said Letters Patent is hereby corrected as shown below:

In the Claims

Column 23, Line 10 please delete "NWT" and insert in its place --MVT--

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*